US007248971B1

(12) United States Patent
Rigoutsos et al.

(10) Patent No.: US 7,248,971 B1
(45) Date of Patent: Jul. 24, 2007

(54) METHOD AND APPARATUS FOR DISCOVERING PATTERNS IN A SET OF SEQUENCES

(75) Inventors: Isidore Rigoutsos, Astoria, NY (US); Yuan Gao, Croton on Hudson, NY (US); Aristidis Floratos, Long Island City, NY (US)

(73) Assignee: International Business Machines Corporation, Armonk, NY (US)

( * ) Notice: Subject to any disclaimer, the term of this patent is extended or adjusted under 35 U.S.C. 154(b) by 1294 days.

(21) Appl. No.: 09/712,638

(22) Filed: Nov. 14, 2000

(51) Int. Cl.
*G01N 33/48* (2006.01)
(52) U.S. Cl. .......................................... 702/20; 702/19
(58) Field of Classification Search .................. 702/20, 702/19
See application file for complete search history.

(56) References Cited

OTHER PUBLICATIONS

Benson et al., Nucleic Acid Research, vol. 25, pp. 1-6, 1997.*
Kleffe et al., Bioinformatics, vol. 14, pp. 232-243, 1998.*
NCBI, NCBI News, pp. 1-18, Aug. 1996.*
Altschul et al., Journal of Molecular Biology, vol. 215, pp. 403-410, 1990.*
JCBN, Amino Acids and Peptides Home Page, pp. 1-10, 1983.*
Wu et al., Bioinformatics, vol. 16, No. 3, 2000, pp. 233-244.*
Stormo, G., Bioinformatics, vol. 16, No. 1, 2000, pp. 16-23.*
Attwood et al., "The PRINTS Protein Fingerprint Database in its Fifth Year," Nucleic Acids Res., 26(1):304-308, (1998).
Bailey et al., "The Value of Prior Knowledge in Discovering Motifs with MEME," In Proceedings of the Third International Conference on Intelligent Systems for Molecular Biology (ISMB '95), Menlo Park, California, AAAI Press, (1995).
Bairoch et al., "The PROSITE Database, its Status in 1997," Nucleic Acids Res., 25(1):217-221, (1997).
Bork et al., "Applying motif and Profile Searches," Methods Enzymol., 266:162-184, (1996).
Gao et al, "Motif Detection in Protein Sequences," In Proceedings of SPRIRE'99, 63-72, (1999).
Grundy et al., "Meta-MEME: Motif-based Hidden Markov Models of Protein Families," Computer Applications in the Biological Sciences (CABIOS), 13:397-406, (1997).

(Continued)

*Primary Examiner*—Cheyne D. Ly
(74) *Attorney, Agent, or Firm*—Ryan, Mason & Lewis, LLP

(57) ABSTRACT

Generally, the present invention provides a way of determining in an unsupervised manner additional members for a family that is defined initially through exemplar sequences. The present invention is unsupervised in that it proceeds without any information related to the exemplar sequences defining the family, without aligning the sequences, without prior knowledge of any patterns in the exemplar sequences, and without knowledge of the cardinality or characteristics of any features that may be present in the exemplar sequences. In one aspect of the invention, a method is used to take a set of unaligned sequences and discover several or many patterns common to some or all of the sequences. These patterns can then be used to determine if candidate sequences are members of the family. In another aspect of the invention, a method is used to take a set of sequences and to determine a set of maximal patterns common to a number of sequences. The maximal patterns are determined without any previous knowledge about any properties or features that may be present in the processed sequences.

13 Claims, 3 Drawing Sheets

OTHER PUBLICATIONS

Henikoff et al., "Blocks Database and its Applications," Methods Enzymol., 266:88-105, (1996).

Nevill-Manning et al., "Highly Specific Protein Sequence Motifs for Genome Analysis," Proc. Natl. Acad. Sci. USA, 95(11):5865-5871, (1998).

Ogiwara et al., "Construction of a Dictionary of Sequence Motifs that Characterize Groups of Related Proteins," Protein Eng., 5(6):479-488, (1992).

Rigoutsos et al., "Dictionary Building Via Unsupervised Hierarchical Motif Discovery In the Sequence Space Of Natural Proteins," Proteins: Structure, Function and Genetics, 37(2): 264-277, (1999).

Saqi et al., "Identification of Sequence Motifs from a Set of Proteins with Related function," Protein Engineering, 7(2):165-71, (1994).

Sonnhammer et al., "Pfam: A Comprehensive Database of Protein Domain Families Based on Seed Alignments," Proteins, 28(3):405-420, (1997).

Tatusov et al., "A Genomic Perspective on Protein Families," Science, 278(5338):631-637, (1997).

Altschul et al., "Basic Local Alignment Search Tool," Academic Pres Limited, J. Mol. Biol. 215, pp. 403-410 (1990).

Altschul et al., "Issues in Searching Molecular Sequence Databases," Nature Genetics, 6:119-129 (Feb. 1994).

Califano et al., "FLASH: A Fast Look-Up Algorithm for String Homology," Proceedings 1993 IEEE Computer Society Conference on Computer Vision and Pattern Recognition, New York, pp. 353-359 (Jun. 15-18, 1993).

Coulson et al., "Protein and Nucleic Acid Sequence Database Searching: A Suitable Case for Parallel Processing," The Computer Journal, vol. 30, No. 5, pp. 420-424 (1987).

Lipman et al., "Rapid and Sensitive Protein Similarity Searches," Science, vol. 227, No. 4693, pp. 1435-1441 (Mar. 22, 1985).

Neuwald et al., "Detecting Patterns in Protein Sequences," Academic Press Limited, J. Mol. Biol. 239, pp. 698-712 (1994).

Pearson et al., "Improved Tools for Biological Sequence Comparison," Proc. Nat'l Acad. Sci. USA, vol. 85, pp. 2444-2448 (Apr. 1988).

Rigoutsos et al., "Combinatorial Pattern Discovery in Biological Sequences: The TEIRESEAS Algorithm," Oxford University Press, Bioinformatics, vol. 14, No. 1, pp. 5-67 (1998).

Rigoutsos et al., "Motif Discovery Without Alignment or Enumeration," RECOMB, New York, pp. 221-227 (1998).

Suyama et al., "Searching for Common Sequence Patterns Among Distantly Related Proteins, Protein Engineering, vol. 8, No. 11, pp. 1075-1080 (1995).

Yamaguchi et al., "Protein Motif Discovery from Amino Acid Sequences by Sets of Regular Patterns," Academic Publications, Information Research Report, 95(76):95-FI-38 (Jul. 1995).

"Part II, Sequence Analysis," Chapter 9, Pattern Discovery, pp. 130-169 (Sep. 1993).

\* cited by examiner

METHOD AND APPARATUS FOR DISCOVERING PATTERNS IN A SET OF SEQUENCES

FIELD OF THE INVENTION

The present invention relates to sequences of symbols and, more particularly, to unsupervised building and exploitation of composite descriptors.

BACKGROUND OF THE INVENTION

Sequences of symbols are useful in a number of areas. One such area is DNA. DNA (deoxyribonucleic acid) may be described through a long sequence of symbols. DNA is commonly described through the characters A, G, C, or T. These characters may be thought of as the alphabet of DNA. Another area where sequences of symbols are important is proteins. Proteins are sequences of amino acids, where each amino acid can be described by a character or letter. The "alphabet" of amino acids comprises the characters of A, C, D, E, F, G, H, I, K, L, M, N, P, Q, R, S, T, V, W, and Y. Sequences of symbols are also important in encryption and coding. For example, computers commonly store character data in numeric format. For instance, the word "the" could be coded in the American Standard Code for Information Interchange (ASCII) format as decimal symbols 116, 104, and 101. Encryption schemes change these numbers to conceal the underlying information.

For amino acids, there are very large databases of knowledge that consist of sequences of proteins. Similar proteins are usually grouped into "families." Family members should have the same properties associated with them; once the properties of one of the family members is known, it is assumed that the other family members will have similar properties. Additionally, once the family is known, the family may be used to determine which candidate proteins are members of the family. Therefore, there has been tremendous research to determine how to best group proteins into families.

Generally, there are four different methods used to group proteins. One method is to determine a pattern of symbols that all of the sequences share. This is called a single descriptor approach, which looks for particular patterns of characters. The patterns are series of expected amino acids, described by alphabetic characters. In the pattern, some locations could be important and some locations might not be. An example pattern for a single descriptor might require certain amino acids to be in one particular location, then allow several "don't care" locations where any amino acid could reside, and then require only a particular amino acid in a final location. The patterns are based on observations that, in nature, specific amino acid positions seem to be preserved in a biased way. These specific amino acids positions are "conserved" even though their neighbors can undergo mutations. Thus, researchers used the concept of conservation to describe the members of the family. A very large, well known database of the single descriptor type is the Prosite database. There are about 1100 families in this database. To find the patterns contained in each family, the proteins contained there were first aligned. Then, the most conserved region of the family was located and the pattern (the single descriptor) contained in all or most of the family members was determined. However, there could be members of a family that did not share the single descriptor. This generates false negatives, as members of the family were incorrectly not discovered as such.

An improvement on the single descriptor method is the composite descriptor method. The composite descriptor method examines a candidate protein for several alphabetic patterns, as opposed to only one pattern with the single descriptor method. Again, this method generally requires aligning the proteins so that the multiple patterns, i.e., the composite descriptor, properly align within their respective blocks.

The conceptual underpinnings are the same across all the methods that rely on composite descriptors. Any differences have essentially to do with either the manner in which multiple alignments are used to construct the descriptors or whether the descriptors are explicitly (e.g., a "regular expression") or implicitly (e.g., a "profile") represented in the composite description. Additional characteristics common to these approaches include: (a) an iterative component; (b) the availability of a set of known (or alleged) family members (="training" set) that provides an initial "bootstrapping" stage; (c) the computation of a multiple-sequence alignment involving members of the training set—these alignments are typically verified manually or semi-automatically and can be used to derive profiles that allow the generation of quality measures when evaluating the results; (d) a range of quality control checks that are optionally applied on the generated results; and, (e) the need to study the collection under consideration in order to identify a minimum set of components that will form the composite description.

There are several problems with these approaches. For instance, in step (c), it is implicitly assumed that there is a multiple-sequence alignment involving all of the members of the training set; the alignment may either be a global alignment of both conserved and non-conserved regions, or a local alignment of the most conserved regions. This requirement unnecessarily burdens these methods. Additionally, multiple alignment programs usually work best when the parameters are optimized for the set of sequences which are being considered.

Steps (d) and (e) presuppose the availability of biological information pertaining to the set under consideration, and this biological information may not always be present. As a matter of fact, step (e) results in the selection and use of features which are conditional on each other. Although easy to describe, an additional assumption here is that the identity, cardinality, and properties of these features are available and also agreed upon ahead of time. For example, a statement such as "G protein-coupled receptors (GPCRs) are proteins involved in signal transduction in eukaryotic organisms that consist of seven transmembrane helices composed typically of hydrophobic amino acids" represents a body of knowledge that has been used by researchers in the building of composite descriptors for GPCRs. With the supervised approaches described above, a detailed and frequently manual study of the collection under consideration is unavoidable.

In addition to descriptor approaches, there are also "windowing" approaches that build descriptors for a family. In these methods, one or more windows are used instead of character patterns. A single window method is called the PROFILE approach. All of the sequences of each of the family members are aligned with respect to their best-conserved region. Researchers then determined a probability distribution for locations in each column of the implied window. For each such block, they determined a probability of expecting an amino acid at some location within the window and thus built a 'profile' of expected probabilities for each of the columns of the window. The researchers would slide this set of probabilities against an unknown protein. If this candidate protein matched the expected probabilities, they included the protein as a member of the family. This approach was more tolerant than the single descriptor approach. Subsequently, researchers began to use profiles for multiple windows. There could be two, three, four windows where the members of the family could agree on content. Sometimes, a profile was not built explicitly but rather was maintained as a collection of the instances across the known or alleged family members of the conserved region under consideration.

The windowing methods again rely on alignment of proteins, which can be relatively complex and computationally lengthy. Typically, these windowing methods are supervised and biological information pertaining to the family can facilitate the analysis. With supervised approaches, a detailed and frequently manual study of the collection under consideration is unavoidable.

Therefore, there exists a need to provide a way of determining and using family members of sequences in an unsupervised manner, without knowledge of biological information related to the family, and without aligning the sequences.

SUMMARY OF THE INVENTION

Generally, the present invention provides a way of determining in an unsupervised manner additional members for a family that is defined initially through exemplar sequences. The present invention is unsupervised in that it proceeds without any information related to the exemplar sequences defining the family, without aligning the exemplar sequences, without prior knowledge of any patterns in the exemplar sequences, and without knowledge of the cardinality or characteristics of any features that may be present in the exemplar sequences. The cardinality of a set is the number of items in a set. For instance, the cardinality of the set of letters in the English alphabet is 26. In one aspect of the invention, a method is used to take a set of unaligned sequences and discover several or many patterns common to some or all of the sequences. These patterns can then be used to determine if candidate sequences are members of the family. In another aspect of the invention, a method is used to take a set of sequences and to determine a set of maximal patterns common to a number of sequences. The maximal patterns are determined without any previous knowledge about any properties or features that may be present in the processed sequences.

A more complete understanding of the present invention, as well as further features and advantages of the present invention, will be obtained by reference to the following detailed description and drawings.

DETAILED DESCRIPTION OF PREFERRED EMBODIMENTS

Figure 1:
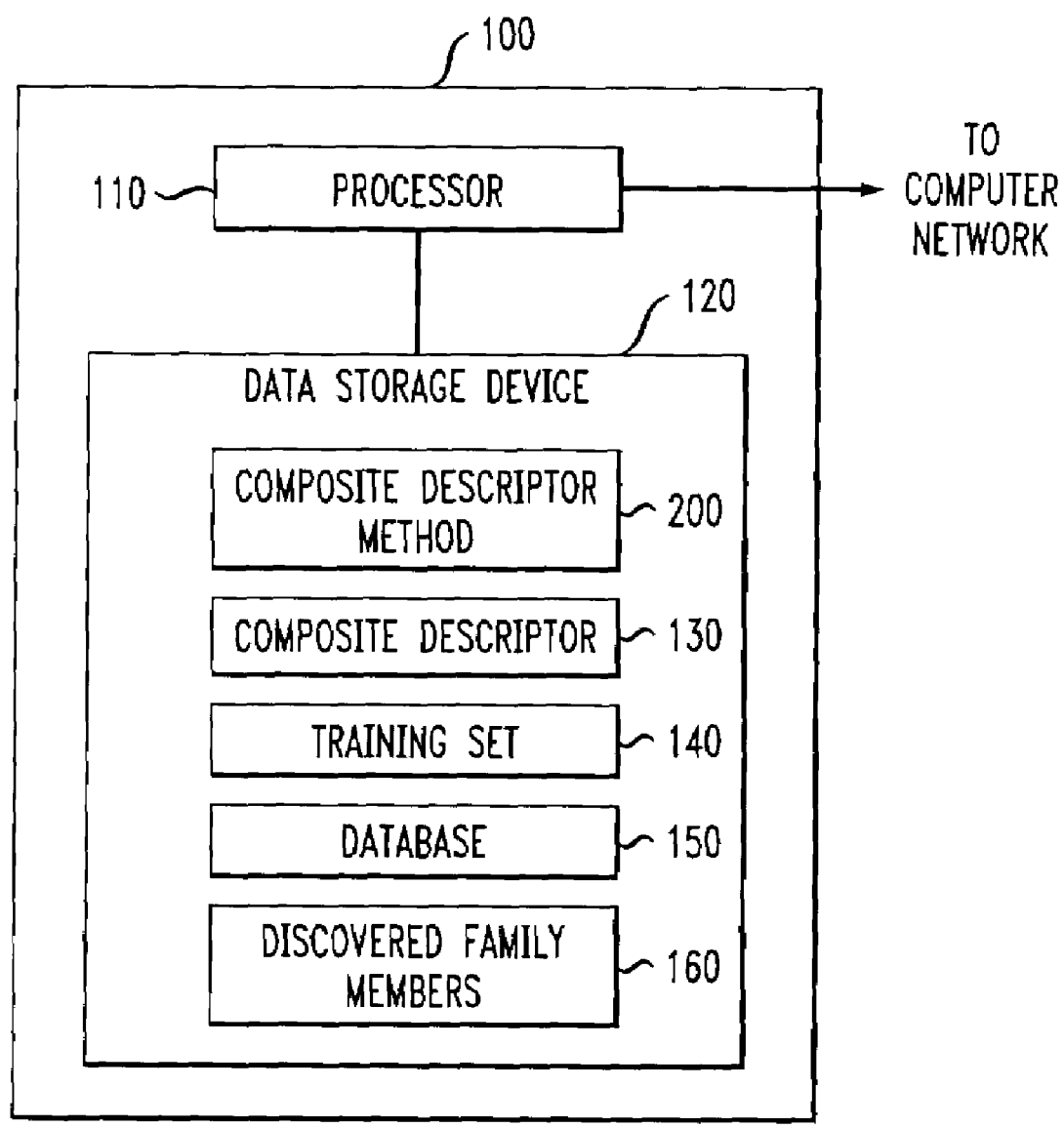
FIG. 1 is a schematic block diagram showing an architecture of a system for unsupervised building and exploitation of composite descriptors in accordance with an embodiment of the present invention.

Generally, the present invention provides a way of determining in an unsupervised manner additional members for a family that is defined initially through exemplar sequences. The present invention is unsupervised in that it proceeds without any information related to the exemplar sequences defining the family, without aligning the sequences, without prior knowledge of any patterns in the exemplar sequences, and without knowledge of the cardinality or characteristics of any features that may be present in the exemplar sequences. The cardinality of a set is the number of items in a set. For instance, the cardinality of the set of letters in the English alphabet is 26. In one aspect of the invention, a method is used to take a set of unaligned sequences and discover several or many patterns common to some or all of the sequences. These patterns can then be used to determine if candidate sequences are members of the family. In another aspect of the invention, a method is used to take a set of sequences and to determine a set of maximal patterns common to a number of sequences. The maximal patterns are determined without any previous knowledge about any properties or features that may be present in the processed sequences.

As previously stated, the present invention provides a way of determining family members in an unsupervised manner. By "unsupervised" it is meant that no predetermined or a priori information is needed/known about the exemplar sequences or is employed by the discovery process. Additionally, there is no need for user supervision or intervention. For instance, the present invention does not require knowledge of biological information related to the family, aligned sequences, knowledge of properties of the exemplary sequences defining the family, and/or knowledge of the cardinality or characteristics of features of the exemplar sequences. It is possible to exclude one or more of the these restrictions. For instance, the present invention could be used on a set of aligned sequences. The present invention would still determine a composite descriptor suitable for examining candidate sequences and either including these sequences in or excluding them from the family. However, a great benefit of the present invention is that it does not need aligned sequences or the knowledge of predetermined properties and features that may be present in the exemplar sequences. Aligning sequences and determining properties and features in the exemplar sequences that originally define the family is time consuming, complex, and at times intractable. Instead, the present invention can determine a composite descriptor without such time intensive efforts.

Concerning features and properties of a sequence of symbols, it is not easy to define what a feature is. The definition of a feature is directly related to the representation of the items that are studied, i.e., the way each of the objects processed by the system under consideration is represented and stored in a computer. Such a representation is in turn related to the way an object can appear in the context of the sensor data, and is unavoidably application specific. For example, in the context of image processing by a computer, the following image characteristics have been used as features: linear and curvilinear segments, curvature extrema, curvature discontinuities, and identifiable conics. In the context of computational biology, an example of a feature can be a combination of amino acids with understood behavior and possibly known 3-dimensional structure. For instance, for a helix-turn-helix (HTH) motif that mediates the binding of many regulatory proteins to regulatory control sites of DNA, the two features are the two helices at the beginning (7 a.a.) and the end (9 a.a.) of the 20 a.a. stretch that corresponds to an instance of the HTH motif. A property can be thought of as an attribute of a feature: in the case of the HTH, a property would be the fact that the two features (helices) are held together through non-polar interactions of their side chains. It should be stressed that the concept of the feature is also intrinsically connected to the task at hand. For example, for some applications, individual a.a. letters can be thought of as "features."

What is important is that previously researchers had to (a) know something about the set of sequences, or (b) align the exemplar sequences, or (c) perform both (a) and (b) before they could determine those motifs that were peculiar to the exemplar sequences and, thus, by extension specific to and characteristic of the family defined by the exemplar sequences. The researchers knew and exploited properties of sequences, knew and exploited features of the sequences, and/or aligned the sequences. The present invention is unsupervised, meaning that no information about the exemplar sequences need be known, and the present invention will still determine patterns that can subsequently be used to define the family implied by the exemplar sequences as well as analyze candidate sequences for inclusion into this family.

In an embodiment of the present invention, a training set of family members is searched in an unsupervised manner to determine statistically significant, common patterns between some or all of the family members. Each family member comprises a sequence, which itself comprises a series of characters. The present invention may be used on any sequence of symbols that can be described as a linear stream of events, e.g., DNA (deoxyribonucleic acid), proteins, languages, and numbers. Preferably, a predetermined sequence-support threshold will initially be set. This predetermined sequence-support threshold determines how many of the sequences in the family need to have a pattern for the pattern to be considered common to the training set. For instance, if there are 100 sequences in the family, the predetermined sequence-support threshold could be set to 50. This means that a pattern must be found in 50 of the sequences for the pattern to be considered common to the family members in the training set. Generally, this threshold is initially set to the number of sequences in the training set. Should no common patterns be found, the sequence threshold may be modified.

If common patterns are found, they are examined to determine if they are statistically significant. Any remaining statistically significant patterns may be used to describe the family members and, subsequently, to ascertain if candidate members are part of the family. Preferably, the statistically significant and common patterns become part of a composite descriptor. Once the statistically significant and common patterns are found for a set (which could include all) of the family members, the sequences containing the patterns are removed from the training set. This results in a smaller training set.

This modified training set is again searched for common patterns. The sequence threshold may be modified to search for fewer sequences of the modified training set or to search for all of the sequences in the training set. If any common and statistically significant patterns are found, the composite descriptor is modified to add the new patterns. This process preferably continues until either all sequences are removed from the training set or until common patterns cannot be found between the remaining sequences.

Once the composite descriptor is determined, the composite descriptor may be used to determine if a candidate sequence is part of the family. In particular, the composite descriptor may be used to search a database of sequences to determine if individual sequences in the database are members of the family described by the composite descriptor. Usually, a pattern-support threshold will be used to make this determination. The pattern-support threshold determines the number of patterns that must match between the candidate sequence and the patterns in the composite descriptor. For example, if there are 1000 patterns in the composite descriptor, the pattern-support threshold may require matches on 995 of the patterns for the candidate sequence to be considered a member of the family. Moreover, after more members of the family are found by using the current composite descriptor, these new members may be added to the original training set to create a new training set. The composite descriptor method may again be run on the new training set. This will provide even greater sensitivity and allow the composite descriptor to "learn" new patterns common to the family.

While the present invention can determine statistically significant and common patterns with aligned sequences, the present invention does not need aligned sequences. To align two sequences, one or more patterns common to both sequences are aligned in a left-to-right order. For example, assume that the pattern being aligned is ABC. The sequence of characters {DEFXYZABC} would be aligned with {ABCDEF} by either aligning the ABC patterns in a left-to-right manner or by aligning the DEF patterns. Thus, when aligning the ABC patterns, the XYZ of the first pattern would not be aligned with characters in the second pattern and the DEF of the second pattern would not align with characters in the first pattern. For this example, there is no unique alignment and it is easy to see how the situation can be complicated further as the number of sequences to process increases. Because the present invention preferably searches for patterns common to the sequences, the present invention would determine that ABC was common to the two sequences, regardless of their alignment.

The present invention also does not need the availability of biological information related to the family. While such information could be used, the present invention will determine statistically significant and common patterns within the family members without biological information. Moreover, because outliers are expected to not contribute much in the way of statistically significant patterns to the composite descriptor, outliers have less of an impact on the present invention.

Turning now to FIG. 1, FIG. 1 is a schematic block diagram showing the architecture of an illustrative system 100 in accordance with the present invention. System 100 may be embodied as a general purpose computing system, such as the general purpose computing system shown in FIG. 1. System 100 includes a processor 110 and related memory, such as a data storage device 120, which may be distributed or local. The processor 110 may be embodied as a single processor or a number of local or distributed processors operating in parallel. Such processors could communicate through a common bus or through one or more networks. The data storage device 120 is operable to store one or more instructions and data, which the processor 110 is operable to retrieve, interpret, execute and use. Data storage device 120, in this example, comprises a composite descriptor method 200, a composite descriptor 130, a training set 140, a database 150, and discovered family members 160. Not all of these need be present at any one time. In general, the composite descriptor method 200 will examine the training set 140 for common and statistically significant patterns. Training set 140 comprises a number of sequences, each of which comprise a series of symbols. Each symbol comes from a collection of possible symbols referred to as an alphabet. The alphabet could describe such entities as DNA (deoxyribonucleic acid) or proteins. The composite descriptor 130 will be modified to add any common and statistically significant patterns that are found. Database 150 contains a number of candidate sequences. Once a composite descriptor 130 is created, the composite descriptor may be used to determine which, if any, of the candidate sequences in the database 150 are part of the family of sequences described by composite descriptor 130. If any candidate sequences are determined to belong to the family, these candidate sequences may be stored in the discovered family members area 160. If desired, the discovered family members 160 may be added to the training set 140 to create a new training set 140. Composite descriptor method 200 may then act on this new training set 140 to further refine composite descriptor 130.

As is known in the art, composite descriptor method 200 may be distributed as an article of manufacture that itself comprises a computer readable medium having computer readable code means embodied thereon. The computer readable program code means is operable, in conjunction with a computer system such as computer system 100, to carry out all or some of the steps to perform the composite descriptor method 200. The computer readable medium may be a recordable medium (e.g., floppy disks, hard drives, Compact Disks, or memory sticks), or may be a transmission medium (e.g., a network comprising fiber-optics, the world-wide web, cables, or a wireless channel using time-division multiple access, code-division multiple access, or other radio-frequency channel). Any medium known or developed that can store information may be used.

Figure 2:
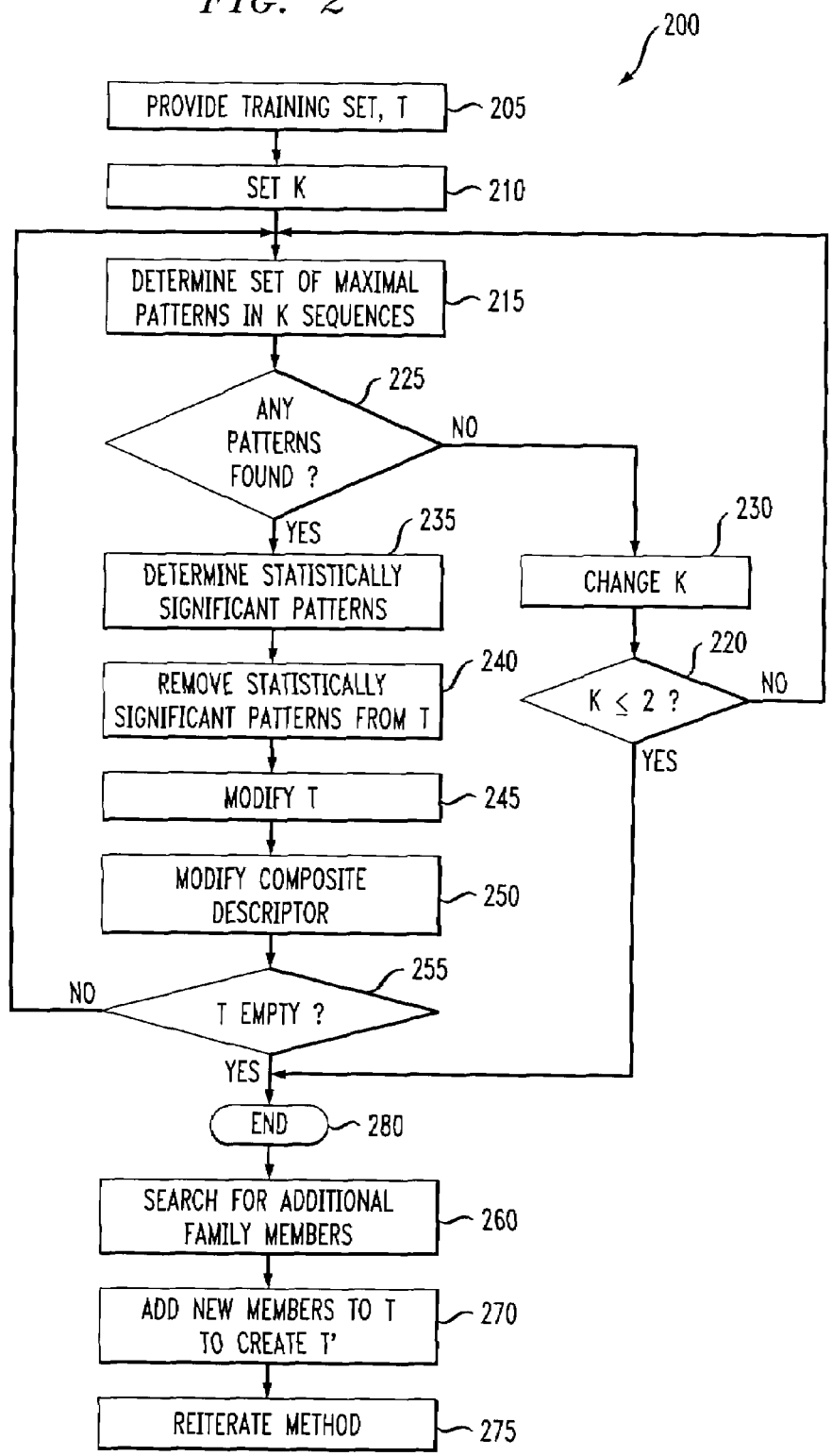
FIG. 2 is flow chart describing unsupervised building and exploitation of composite descriptors employed by the system of FIG. 1.

Composite descriptor method 200, as shown in FIG. 2, performs unsupervised building of composite descriptors and then exploits the determined composite descriptors to find additional family members of the families described by the composite descriptors. Method 200 is performed whenever it is desired that a composite descriptor be determined and used. It should be noted that method 200 may be broken into multiple sections. Preferably, the steps up to step 280 would be used to determine a composite descriptor from a training set, while optional step 260 would be used to apply the composite descriptor to one or more candidate sequences, and optional steps 270 and 275 would be used to further refine the composite descriptor.

Method 200 begins in step 205 when a training set is provided. It should be noted that the sequence of steps are not necessarily in order. The training set, T, is preferably N unaligned sequences $s_i$ for which there is reason to believe that the sequences are related. There should exist identifiable local similarities among members of T at the amino acid level, although it is assumed that no other information is available for the members of T, e.g., known or identifiable secondary structures, known or identifiable domains, functional information, physio-chemical properties, or physical properties. If no identifiable local similarities exist among members of T, method 200 will not provide a suitable composite descriptor for the family, as a composite descriptor does not exist for the family.

Each sequence is a series of symbols from an alphabet. For proteins, one can denote by Σ the alphabet of all amino acids; i.e., Σ={A, C, D, E, F, G, H, I, K, L, M, N, P, Q, R, S, T, V, W, Y}. On this alphabet, regular expressions can be defined that can range from very simple n-grams to more general ones containing wild cards and capturing strings of variable length. The '.' (referred to as the "don't care character") is used to denote a position in a sequence or pattern that can be occupied by an arbitrary residue. A bracket is meant to denote a "one of" choice; i.e., [KR] means that the position this bracket corresponds to can be occupied by exactly one of K or R. A bracket can have a minimum of 2 alphabet characters but not more than |Σ|−1.

In step 210, the sequence threshold, K, is set. It is possible to set K=|T|, which is the number of sequences in the training set. In actuality, it has proven beneficial to assign a small starting value to K that is a fraction of the number of sequences in T. Experiments have shown that a starting value of K=|T|/b with b=4 or 5 is a good choice across many data sets. Note that the smaller the value of b, the higher the redundancy of the composite descriptor will be. The selection of K also can depend on how conserved, or similar, the family members are. If the family members are well conserved, then K can be higher; if the family members are not well conserved, then K can be lower.

In step 215, a set of maximal patterns in the K sequences is determined. In general, this step tries to determine common patterns between the K sequences. Not only should the patterns be common, but they should also be as large as possible. These large patterns may further be mathematically defined as "maximal" in a way described below. Any of the available algorithms which can guarantee that all sought patterns are discovered and that they are maximal can be used here. For the experiments related below, a Teiresias algorithm was used. This algorithm is described in Floratos, et al., U.S. Pat. No. 6,108,666, "Method and Apparatus for Pattern Discovery in 1-Dimensional Systems"; Floratos, et al., U.S. Pat. No. 6,092,065, "Method and Apparatus for Discovery, Clustering and Classification of Patterns in 1-Dimensional Event Streams"; Rigoutsos, I. and A. Floratos, "Combinatorial Pattern Discovery in Biological Sequences: the Teiresias Algorithm," Bioinformatics, 14(1):55-67, 1998; and Rigoutsos, I. and A. Floratos, "Motif Discovery Without Alignment Or Enumeration," Proceedings 2nd Annual ACM International Conference on Computational Molecular Biology, New York, N.Y., March 1998, the disclosures of which are incorporated by reference herein.

A short introduction to this method follows. A pattern S is a regular expression on Σ that defines a language G(S). The elements of the language are all the strings that can be obtained from the regular expression that S stands for. A protein is said to match a given pattern S if and only if it contains at least one substring (i.e., a block of consecutive residues) that belongs in G(S). A pattern S' is said to be more specific than a pattern S if G(S')⊂G(S). Given a pattern S and a database D, an offset list of a pattern of S may be defined with respect to D (or simply the offset list of S, when the database D is unambiguously implied) to be the following set: $L_D(S)=\{(i, j)|$ the i-th sequence of the database D matches the pattern S at offset j}. A pattern S is called maximal with respect to a database D if there exists no pattern S' which is more specific than S and such that $|L_D(S)|=|L_D(S')|$. A maximal pattern cannot be made more specific without simultaneously reducing the cardinality of its offset list. A pattern S is called an <L,W> pattern (with L≦W) if every substring of S with length W contains L or more non-don't care positions. Note that a given choice for the parameters L and W has a direct bearing on the degree of remaining similarity among the instances of the domain that is captured by the regular expression: the smaller the value of the ratio L/W, the higher the degree of sought similarity.

The Teiresias algorithm is a pattern discovery algorithm that can guarantee the discovery of all <L,W> patterns that are maximal and supported by K or more input sequences. The pattern discovery is carried out while allowing the symbols of $\Sigma$ to be partitioned in equivalence classes. Any symbol within a given class is able to replace any other symbol of the (same) class. One such example would be the partition: {A, G}, C, {D, E}, {F, Y}, H, {I, L, M, V}, {K, R}, {N, Q}, P, {S, T}, W. In fact, the various symbol classes do not have to form a partition of $\Sigma$. In other words, a given symbol can belong to more than one class. One such set of classes can be obtained by using a distance threshold with any of the currently available scoring matrices such as the PAM BLOSUM series. PAM is described in Dayhoff, "Atlas of Protein Sequence and Structure," vol. 5, National Biomedical Research Foundation, 1978; and BLOSUM is described in Henikoff, "Amino Acid Substitution Matrices from Protein Blocks," Proc. Natl. Acad. Sci. USA, 89:100915-100919, 1992, the disclosures of which are incorporated by reference.

The Teiresias algorithm permits the discovery of all <L,W> patterns that are maximal and supported by K or more input sequences, in the presence of stated equivalences involving symbols from the input alphabet. Each pattern S that the Teiresias algorithm will discover is of the form:

$$(\tau \cup [\Sigma\Sigma^*\Sigma])(\Sigma \cup [\Sigma\Sigma^*\Sigma] \cup \{.\})^*(\tau \cup [\Sigma\Sigma^*\Sigma]).$$

Associated with each pattern S is the sensitivity of the pattern, which is directly related to the number of sequences in D that contain S. The sensitivity is a measure of how many members of the training set T do not match S (=false negatives). Also associated with S is the pattern's specificity, which is a direct measure of how many members of the database D match the pattern, but are not true members of the collection that the training set T represents (=false positives). The choice of the values for the parameters L and W is a function of the collection under consideration. Experimental work has shown that a choice supporting moderate degree of local similarities (e.g., ~40-50%) is a good choice across a very large variety of test cases.

In step 225, it is determined if any patterns are found. In no patterns are found (step 225=NO), the sequence threshold, T, can be decreased. Preferably, this is done by setting K=|T|/b, where b is usually set to 4 or 5. It is also possible to set b to smaller values, such as 2 or 3. Setting b to smaller values increases the amount of processing time it might take to determine maximal patterns. For instance, if there are 1000 sequences in T and K=|T|=1000, and no common maximal patterns are found, it is necessarily the case that changing K to 999 will not find any common maximal patterns. Changing K from 1000 to 250, however, will make it more likely that common maximal patterns may be found. After K has been changed (step 230), it is determined if K meets a predetermined minimum limit. This limit has been set, in the example of FIG. 2, as 2. If there are two (or even more) sequences that have a pattern, even a maximal pattern, in common, this pattern may not be representative of the family members. In step 220, other minimum sequence-support thresholds may be used, if desired. The choice of the predetermined minimum limit is not critical, as outliers (those sequences that are the "edge" of the family or even not part of the family) are expected to have little or no bearing on the composite descriptor of the present invention. This is discussed in more detail below, in reference to step 260.

If maximal patterns are found in step 215 (step 225=YES), in step 235, it is determined if the maximal patterns are statistically significant. In general, in step 235, it is determined, for each maximal pattern, what the probability is that the maximal pattern occurs in a sequence. This probability should meet a predetermined threshold. This step is important because the patterns will be exploited, as part of the composite descriptor, to determine additional family members. If relatively general patterns are used, the patterns could include candidate members into a family when the candidate members are not members of the family. For instance, for the English language, the pattern "the" is much more likely to appear in a sentence than is the pattern "quit." The pattern "the" would be much more likely to include candidate members as part of the family than would the pattern "quit." This would be appropriate if the family was defined as any sentence having the pattern "the." However, a much more likely occurrence is to define a sentence as any sentence having the pattern "quit," and if the pattern "the" is used as part of a composite descriptor, it is possible that this pattern will generate too many false family members.

From the set of maximal <L,W> patterns that are discovered, the set $M_S$ is selected that contains only those that are statistically significant. With appropriate modifications, any of several published methods can be used at this step, the disclosures of which are herein incorporated by reference: Atteson, "Calculating the Exact Probability of Language-like Patterns in Biomolecular Sequences," Proceedings of the Sixth International Conference on Intelligent Systems for Molecular Biology (ISMB '98), Menlo Park, Calif., AAAI Press, 1998; Jonassen, ICollins, and Higgins, "Finding Flexible Patterns in Unaligned Protein Sequences," Protein Science, pp. 1587-1595, 1995; Nicodeme, Salvy and Flajolet, "Motif Statistics," INRIA Technical Report No 3606, January 1999; Pevzner, Borodovksi and Mironov, "Linguistic of Nucleotide Sequences: the Significance of Deviation from Mean Statistical Characteristics and Prediction of the Frequencies of Occurrences of Words," Journal of Biomolecular Structure Dyn., 6:1013-1026, 1989; Regnier, "A Unified Approach to Word Statistics," Proceedings 2nd Annual ACM International Conference on Computational Molecular Biology, New York, N.Y., March 1998; Sagot, and Viari, "A Double Combinatorial Approach to Discovering Patterns in Biological Sequences," Proceedings of the Seventh Symposium on Combinatorial Pattern Matching, pp. 186-208, 1996; Sewell and Durbin, "Method for Calculation of Probability of Matching a Bounded Regular Expression in a Random Data String," Journal of Computational Biology, 2(1):25-31, 1995; and Wooton, "Evaluating the Effectiveness of Sequence Analysis Algorithms Using Measures of Relevant Information," Computers Chem., 21(4):191-202, 1997.

For simplicity, the probabilities of the discovered patterns, as disclosed in the Examples section below, were determined with the help of a 2nd order Markov chain method, as described in Salzberg, Delcher, Kasif, and White, "Microbial gene identification using interpolated Markov models," Nucleic Acids Res., 26(2):544-8, 1998, which is incorporated herein by reference. The natural logarithm of the estimated probability was used as the measure of a pattern's significance. This threshold can be estimated as a function of the size of the database to be searched with the composite descriptor.

The cardinality of the sub-selected set $M_S$ of patterns ought to be high because of the redundancy of sequence segments from T that are captured by the patterns. This will guarantee a strong signal-to-noise ratio when the composite descriptor is used as a predicate. It is worth pointing out at this point that even if the training set has just a few members, the cardinality of $M_S$ (and thus the redundancy) can be high since there is a multitude of patterns that one can generate even from a few sequences.

Once the statistically significant patterns are found, these patterns are removed from the training set, T, of sequences. This occurs in step 240. It should be noted that steps 240, 245 and 250 do not have to occur in this order and could even occur in parallel. Preferably, each sequence of the training set is examined to determine whether it matches any of the significant patterns of $M_S$. After all patterns of $M_S$ have been exhausted, all sequences that matched one or more patterns are added to a temporary set A. Upon completion of the iteration, one or more sequences from T will have been entered into the set A; these are essentially the sequences that have been accounted for. What remains of T after the removal of these sequences, i.e., T\A, is used as the training set for the next iteration. Thus, the training set T is modified (step 245), which could include marking which sequences in an array of sequences are no longer valid, or copying the remaining sequences into a new array.

In step 250, the composite descriptor is modified. Preferably, the composite descriptor is a union of the composite descriptor and the set $M_S$. The set of significant patterns $M_S$ which was discovered during this last iteration is added to the composite descriptor by adding those patterns in $M_S$ that are currently not in the composite descriptor.

In step 255, it is determined if the training set, T, is empty. If the training set is not empty (step 255=NO), the method continues in step 215 and repeats. If the training set is empty (step 255=YES), and after step 220=YES, the method ends in step 280. Optionally, Steps 260, 270 and 275 may be performed at this point.

At the end of this stage, the composite descriptor contains a set of patterns that by design are specific and sensitive for the collection that the training set T represents. Several properties distinguish this composite descriptor from previous collections of patterns, such as the Prints database of patterns. For example, the building of the composite descriptor is automatic, it does not require manual intervention and does not necessitate the computation of multiple alignments. Additionally, there is no need for biological knowledge specific to the training set T that will impose helpful constraints during generation of the composite descriptor. Also, highly similar sequences need not be removed from the training set prior to the building of the composite descriptor. Additionally, as discussed below in reference to step 260, the training set can safely contain a small percentage of potential outliers, i.e., sequences that have questionable membership in the collection that the training set represents. Because of the redundant, iterative nature of the building phase, the resulting composite descriptor is not expected to contain any statistically significant patterns that are shared by both the outliers and the rest of the sequences in T. Through the initial selection of the support value (small K) the composite descriptor can be made sensitive and contain patterns that are specific for the set T (i.e., large probability threshold, $Thr_{prob}$). Finally, the fact that the composite descriptor contains all those patterns which are specific, significant, and which by design account for every member of the training set, guarantees a strong signal-to-noise ratio when using composite descriptor as a multi-valued predicate (which takes place in step 260). Steps 205 through 255 may be expressed in pseudo-code as follows.

```
i)    CompDescr ← ø
ii)   K ← |T| (or K ← max(2, |T|/b) - see also text)
iii)  discover the set M of all <L,W> maximal patterns in T
      that are supported by at least K sequences of T
iv)   if (|M| = 0) then
            if (K == 2) terminate;
            set K ← K-1 (or K ← max(2, K/b)
          continue with step iii)
      end-if
```

In step 260, the composite descriptor is exploited to determine if candidate sequences are members of the family described by the composite descriptor. Generally, a database of sequences (such as database 150 of FIG. 1) will be searched, but individual sequences may also be compared against the composite descriptor. The composite descriptor will be a number of common, statistically significant and maximal patterns that describe the family. As such, the composite descriptor acts much like a dictionary to describe the family. It can be used in step 260 to determine additional members of the family.

Because method 200 relies on searching through a family and determining the common, statistically significant and maximal patterns that compose the composite descriptor, outliers tend not to matter as much for the present invention. An outlier is a sequence that has been erroneously included within the family. Some simple examples will help to explain why outliers are not a hindrance to the present invention.

Assume that there are 100 members of the family; assume also that 93 members of the family are accounted for but there are 7 outliers that were erroneously included as members of the family. Since, by definition, the latter set comprises the outliers, it is generally true that the number of patterns that will be shared among them and the remaining 93 sequences should be very small (if not 0) when compared to the number of patterns that will be shared by the 93 truly related sequences. This will thus generate very small (if any) support for sequences that are not true members of the family being studied. Moreover, these erroneous patterns will be further filtered out through the statistical significance filtering stage. Finally, when the composite descriptor, which contains patterns common to all 100 sequences, is used to determine if a new sequence is part of the family, the composite descriptor will be used with a pattern-support threshold. In other words, there will be some minimum number of patterns that the new sequence must have in order to be considered part of the family. This threshold will usually be high enough such that outliers, even if they contribute patterns, will not cause non-family members to be included within the family.

In step 260, the composite descriptor can be used as a multi-valued predicate that can determine the membership of a query sequence in the collection that the original training set T defines. The composite descriptor can be used to examine a candidate-for-membership-in-T sequence $S_{cand}$ for instances of the permitted patterns. Given $S_{cand}$, as many local counters as the length of the sequence may be allocated and initialized to 0. A global counter for the sequence may also be allocated and also initialized to 0. If it is determined that a segment of the query matches a pattern m, the local counters at the sequence positions matching the pattern are incremented by an amount equal to d. The possible choices for d include among others "the number of occurrences $o_m$ of m in T" and "the number 1." The former choice favors segments that match patterns supported by a lot of sequences in T whereas the latter gives comparatively increased support to segments that are only moderately conserved. The choice for the amount d by which to increment the local counters modifies the semantics of the predicate's output value.

If the value of d is set to '1' then the predicate is a measure of how many distinct patterns generated from T are matched by the query sequence. In this case, large values indicate that the result is corroborated by multiple patterns which are specific for the collection T. Smaller values are at the very minimum indicative of the existence of local similarities that are shared by the query and one or more members of the training set T. Such similarities can imply one of two things: either the query is a true but distant member of the collection under consideration or it is not a true member but it nonetheless shares one more regions of similarity with members of the collection.

If the value of d is set to 'the number of occurrences' of the respective pattern in the training set T, the predicate is a measure of how many distinct sequence fragments in T are similar to the respective query fragment. Large values indicate regions that are shared by a large number of sequences in T and can be indicative of a conserved active site, for example. Both choices of d have merit and the one to use depends on the task at hand.

Independent of what the choice for d is, every time a segment of $S_{cand}$ matches a pattern m, the global counter associated with $S_{cand}$ is incremented by d. After all of $S_{cand}$ have been examined, the values of the global counter are inspected for $S_{cand}$; if they exceed $Thres_{rand}$, $S_{cand}$ is reported as a candidate for membership in the collection defined by T.

The value of $Thres_{rand}$ depends on the actual contents of the composite descriptor and can be determined as follows: beginning with the composite descriptor that was built from the training set T, one can scan as outlined above a randomized version of a very large database such as GenPept or Swiss-Prot. Essentially, each sequence of such a database is treated as a potential query. Upon completion of the scanning process, one can accumulate support for all the sequences that matched one or more patterns of the composite descriptor and histogram the support values to obtain their distribution. The value of $Thres_{rand}$ may be determined by identifying the q-th percentile of this last distribution. Typically, q is set to 95 or higher.

After step 260 has been performed, it is possible to take the new members found and add them to a new training set that comprises the old training set and the new members. Then steps 205 through 280 may be run again (step 275) to further refine the composite descriptor for this family. Thus, the present invention allows learning to be performed, if this is desired.

The present method does not suffer from drawbacks related to (a) the need for good multiple sequence alignments, (b) the inclusion of outliers, (c) the inherent dependence of the results on the selection of the scoring matrix that is used, and (d) overtraining. Indeed, building of the composite descriptor does not require the computation of any multiple sequence alignments, whereas the redundancy of representation that is inherent in composite descriptor is expected to more than counterbalance the inclusion of any small number of outliers. Additionally, this will prevent the system from including even more outliers during the following iteration. Moreover, after each iteration, only the sequence fragments whose support exceeds threshold are considered thus allowing the process to remain 'focused' on what has been deemed important and relevant for the dataset under consideration.

Finally, it should be noted that the training set T, which is given at the very beginning of this iterative process, impacts on the quality of the results (i.e., sensitivity and specificity) that the method will produce. For example, if the original training set is not sufficiently representative of all instances of a family's members (e.g. GPCRs), or of the construct of interest (e.g. the helix-turn-helix DNA binding motif), the generated composite descriptor should not be expected to discover all instances relating to the training set. This last observation holds true for all methods that try to build single or composite descriptors by starting with a training set T. Since the augmented training sets at the beginning of the i+1-st iteration preferably only comprise the sequence fragments which exceeded threshold during the i-th iteration, the composite descriptor will maintain its 'focus' on what is essentially dictated by the original training set. That is not to say that that the composite descriptor will not be sensitive; on the contrary, the composite descriptor will be sensitive to the extent that the processed data permit while at the same time remaining in lock-step, so to speak, with the originally provided training input. As a matter of fact, the experimental results discussed below on three specific datasets demonstrate that even starting with small training sets allows discovery of a large number of representatives of the same group.

EXAMPLES

Now that the method and apparatus have been described, some exemplary results are shown in this section. In this section, results are described from the building and use of composite descriptors for three distinct collections of data. The collections were chosen in such a way so as to showcase the ability of the present invention to handle input sets across a variety of contexts.

The first collection comprises sequences from PROSITE entry PS50040 of elongation factor 1 gamma chain sequences; in Release 15.0 of the PROSITE database, only a matrix profile is available for this collection.

The second collection comprises complete sequences as well as fragments of G protein-coupled receptors, a very important and diverse family of proteins that has traditionally been used as a benchmark test for gauging the quality of pattern-based approaches.

Finally, the third collection comprises sequence fragments that are known to contain an instance of the helix-turn-helix DNA binding motif, a structural motif of great importance.

First, the composite descriptors were built for each of the three collections and evaluated by treating the sequences in Swiss-Prot Release 38.0 as candidates for membership in each of the respective three collections.

Once the behavior of the descriptors is characterized in the context of Swiss-Prot, the 19,099 ORFs were searched in the complete genome of *Caenorhabditis elegans* and these results reported below.

Before proceeding, here are some methodological details and parameter choices that are common in all three cases. In particular, the value d, by which the counters are incremented, is set to 1, essentially favoring those sequences that contain more instances of distinct patterns over others. The value of $Thr_{prob}$ is determined by assuming that the patterns ought to be able to discriminate among sequences in a database as large as GenPept; although for a database of this size an estimated log-probability of −25 or less ought to suffice. Thus, the more stringent threshold of $Thr_{prob}=-30$ was used with the understanding that this will result in a sacrifice in sensitivity. But as the results will demonstrate, even with this stringent threshold, the redundancy of each composite descriptor leads to a sensitivity that is satisfactory. Also, in all three cases the following a.a. equivalences are assumed: {A, G}, C, {D, E}, {F, Y}, H, {I, L, M, V}, {K, R}, {N, Q}, P, {S, T}, W.

The First Example

EF1G/PS50040

An application of the above described methodology is in the context of the PROSITE database. Although numerous entries in PROSITE contain succinct and specific patterns capturing most or all of the members of the corresponding collection, there exist entries for which only a profile/matrix is available: PS50040, the family of elongation factor 1 gamma chain proteins is one such example thus making it an ideal candidate for processing with the described method.

PS50040 comprises 10 full sequences (EF1G_ARTSA, EF1G_CAEEL, EF1G_HUMAN, EF1G_RABIT, EF1G_SCHPO, EF1G_TRYCR, EF1G_XENLA, EF1G_YEAST, EF1H_XENLA, EF1H_YEAST) and 1 fragment (EF1G_PIG). The reported profile matrix captures all 10 full sequences, misses the one fragment and generates no false positives when the target database is Swiss-Prot Rel. 38.0.

It should be noted here that if one relaxes the constraints imposed by the chemical equivalence classes shown above, it is possible to discover a specific pattern that belongs to all 11 members of PS50040 and generates no false positives when used in conjunction with Swiss-Prot Rel. 38.0. In fact, this pattern is

[ILMV]..[NW][ILMV]..[AG]...[RI][ILMV]...[KT]..F....[ILMV].[GH]........[AG]

and can be used to describe and capture elongation factor 1 gamma chain proteins; the deviations from the above chemical equivalence classes are shown in boldface.

The composite descriptor was built for this collection by setting the Teiresias parameters to L=5 and W=10; since the dataset is small there was only a single iteration over the dataset with a threshold choice of K=6. In other words, the composite descriptor was built by discovering patterns that involved a minimum of 5 non-wild cards in any rolling window that spans 10 positions and begins/ends with a literal, a relatively high-degree of local similarity (i.e. 50% or higher). Those patterns whose estimated log-probability was equal to −30.0 or less were selected and this generated a composite descriptor that comprised 2,260 patterns.

First, a corresponding DFA (deterministic finite automaton, which will only recognize instances of the composite descriptor patterns in a query sequence and which performs method step 260) was used to search a randomized version RAND-Swiss-Prot of Swiss-Prot (Release 38.0) that was obtained by applying a randomly chosen permutation to the amino acids of each of the valid sequences. Both the composition and lengths of individual sequences were maintained by this operation. The global counter for each randomized sequence was derived by summing up the local counters from each sequence region that received non-zero support. The sequences were then sorted in order of decreasing global-counter value. Twenty seven (27) randomized sequences received non-zero support with global counter values that ranged between 1 and 2 inclusive. $Thres_{rand}$ was thus set to 3, and the DFA was subsequently used to search the actual Swiss-Prot database. Of the 69 sequences that received non-zero support, only 16 exceeded the predefined threshold. The support values for the 16 sequences were: EF1G_HUMAN 861, EF1G_RABBIT 846, EF1G_XENLA 791, EF1H_XENLA 765, EF1G_ARTSA 349, EF1G_CAEEL 228, EF1G_YEAST 110, EF1G_SCHPO 110, EF1H_PIG 96, EF1H_YEAST 94, EF1G_TRYCR 88, SYV_FUGRU 7, GTT1_RAT 5, GTT1_MOUSE 5, SYEP_HUMAN 3 and GTH4_MAIZE 3.

Note that the 5 hits SYV_FUGRU, GTT1_RAT, GTT1_MOUSE, SYEP_HUMAN and GTH4_MAIZE are clearly separated from the 11 top scoring sequences. They however obtained scores which were above threshold and thus are studied in more detail. In all 5 cases, one or more sizeable regions that were shared with one or more members of the PS50040 collection were discovered. The Clustal-W alignment of EF1G_XENLA and the N-terminus of SYV_FUGRU, a valyl-trna synthetase from *Fugu rubripes*, are shown in Table 1 below. Table 1 shows a Clustal-W alignment of EF1G_XENLA and the N-terminus of SYV_FUGRU, and this shows a strong similarity. As can be seen, the similarity among these two sequences is pretty extended and the Clustal-W score for the shown alignment equaled 462.

Similar shared regions are present in GTT1_RAT & GTT1_MOUSE (a glutathione s-transferase 5 from *Rattus norvegicus* and a glutathione s-transferase theta 1 from *Mus musculus* respectively), SYEP_HUMAN (a multi-functional aminoacyl trna-synthetase from *Homo sapiens*) and GTH4_MAIZE (a glutathione s-transferase IV from *Zea mays*). The Clustal-W alignments for these cases are shown in Tables 2 through 4 below. Table 2 shows a Clustal-W alignment showing a substantial similarity between GTT1_RAT, GTT1_MOUSE and EF1G_ARTSA. The Clustal-W score is 1577. Table 3 shows a Clustal-W alignment between a fragment from EF1G_CAEEL (a.a. 100 through 243) and a fragment from SYEP_HUMAN (a.a. 1 through 180) showing a shared region. The Clustal-W score for this alignment is 74. Table 4 shows a Clustal-W alignment showing a strong similarity between EF1G_RABIT and GTH4_MAIZE. The Clustal-W score is 215.

It should be noted that a search of MEDLINE has indicated that with the exception of the similarity between the EF1G family and the valyl-tRNA from *Fugu rubripes*, none of the other similarities shown here has been reported in the literature.

In summary, the composite descriptor has correctly picked out the members of PS50040 from the contents of Swiss-Prot as well as has identified several substantial similarities with other sequences in the database.

TABLE 1

| | | |
|---|---|---|
| EF1G_XENLA | (SEQ ID NO 1) | MAGGTLYTYPDNWRAYKPLIAAQYSGFPIKVASSAPEFQFGVTNKTPEFLKKFPLGKVPA |
| SYV_FUGRU_piece | (SEQ ID NO 2) | MA--TLYVSP------------HLDDFRSLLALVAAEY---------------------- |
| | | ** ***. * : ..* :* *.*: |
| EF1G_XENLA | (SEQ ID NO 3) | FEGKDGFCLFESSAIAHYVGNDELRGTTRLHQAQVIQWVSFSDSHIVPPASAWVFPTLGI |

TABLE 1-continued

| | | |
|---|---|---|
| SYV_FUGRU_piece | (SEQ ID NO 4) | -------C------------GNAKQ-------QSQVWQWLSFADNELTPVSCAVVFPLMGM |
| | |        *           ** :      *.** *:**:*...:.* :.* *** :*: |
| EF1G_XENLA | (SEQ ID NO 5) | MQYNKQATEQAKEGIKTVLGVLDSHLQTRTFLVGERITLADITVTCSLLWLYKQVLEPSF |
| SYV_FUGRU_piece | (SEQ ID NO 6) | TGLDKKIQQNSRVELMRVLKVLDQALEPRTFLVGESITLADMAVAMAVLLPFKYVLEPSD |
| | | :*: :::: : ** ***. *:.******* *****:*:* ::* :* ***** |
| EF1G_XENLA | (SEQ ID NO 7) | RQPFGNVTRWFVTCVNQPEFRAVLGEVKLCDKMAQFDAKKFAEMQPKKETPKKEKPAKEP |
| SYV_FUGRU_piece | (SEQ ID NO 8) | RNVLMNVTRWFTTCINQPEFLKVLGKISLCEKMVPVTAKTSTEEAAAVH-PDAAALNGPP |
| | | *: : ****.:*** *::.:. . **. :* . . *. * |
| EF1G_XENLA | (SEQ ID NO 9) | KKEKEEKKKAAPTPAPAPEDDLDESEKALAAEPKSKDPYAHLP-KSSFIMDEFKRKYSNE |
| SYV_FUGRU_piece | (SEQ ID NO 10) | KTEAQLKKEAKKREKLEKFQQKKEMEAKKKMQPVAEKKAKPEKRELGVITYDIPTPSGEK |
| | | *.* : **:* :: .* * :* ::. : ..* :: .:: |
| EF1G_XENLA | (SEQ ID NO 11) | DTLTVALPYFW-EHFDKEGWSIWYAEY-KFPEELTQAFMSCNLITGMFQR-LDKLRKTGF |
| SYV_FUGRU_piece | (SEQ ID NO 12) | KDVVSPLPDSYSPQYVEAAWYPWWEKQGFFKPEFGRKSIGEQNPRGIFMMCIPPPNVTGS |
| | | . :. .** : :: :.* *: : * *: : :. : *:* : . ** |
| EF1G_XENLA | (SEQ ID NO 13) | ASVILFGTNNNSSISGVWV-FRGQDLAFTLSED-----WQIDYESYNWRKLDSGSEEC-- |
| SYV_FUGRU_piece | (SEQ ID NO 14) | LHLGHALTNAIQDTLTRWHRMRGETTLWNPGCDHAGIATQVVVEKKLMREKGTSRHDLGR |
| | | : ** .. * :**: :. . * *: *. *: .:. .: |
| EF1G_XENLA | (SEQ ID NO 15) | KTLVKEYFAWEGE--------FKNVGKPFNQG-KIFK----------------------- |
| SYV_FUGRU_piece | (SEQ ID NO 16) | EKFIEEVWKWKNEKGDRIYHQLKKLGSSLDWDRACFTMDPKLSYAVQEAFIRMHDEGVIY |
| | | :.::::* : *:.* :*::*..:: . *. |

TABLE 2

| | | |
|---|---|---|
| GTT1_MOUSE | (SEQ ID NO 17) | -VLELYLDLLSQPCRAIYIFAKKNNIPFQMHTVELRKGEHLSDAFARVNPMKKVPAMM-D |
| GTT1_RAT | (SEQ ID NO 18) | -VLELYLDLLSQPCRAIYIFAKKNNIPFQMHTVELRKGEHLSDAFAQVNPMKKVPAMK-D |
| EF1G_ARTSA | (SEQ ID NO 19) | VAGKLYTYPENFRAFKALIAAQYSGAKLEIAKSFVFGETNKSDAFLKSFPLGKVPAFESA |
| | | . :** . . * *: .. ::: : : **** : *: ****: |
| GTT1_MOUSE | (SEQ ID NO 20) | GGFTLCESVAILLYLAHK-----------------------YKVPDHWYPQDLQARARV |
| GTT1_RAT | (SEQ ID NO 21) | GGFTLCESVAILLYLAHK-----------------------YKVPDHWYPQDLQARARV |
| EF1G_ARTSA | (SEQ ID NO 22) | DGHCIAESNAIAYYVANETLRGSSDLEKAQIIQWMTFADTEILPASCTWVFPVLGIMQFN |
| | | .*. :.** ** *:*:: .. * * |
| GTT1_MOUSE | (SEQ ID NO 23) | DEYLAWQHTGLRRSCLRALWHKVMFPVFLGEQIPPETLAATLAELDVNLQVLEDKFLQDK |
| GTT1_RAT | (SEQ ID NO 24) | DEYLAWQHTTLRRSCLRTLWHKVMFPVFLGEQIRPEMLAATLADLDVNVQVLEDQFLQDK |
| EF1G_ARTSA | (SEQ ID NO 25) | KQATARAKEDIDKALQALDDHLLTRTYLVGERITLADIVVTCTLLHLYQHVLDEAFRKSY |
| | | .: * : : :: * : . ::**:* :...* : *.: :**:: * :. |
| GTT1_MOUSE | (SEQ ID NO 26) | DFLVGPHISLADLVAITELMHPVGGGCPVFEGHPRLAAWYQRVEAAVGKDLFREAHEVIL |
| GTT1_RAT | (SEQ ID NO 27) | DFLVGPHISLADVVAITELMHPVGGGCPVFEGRPRLAAWYRRVEAAVGKDLFLEAHEVIL |
| EF1G_ARTSA | (SEQ ID NO 28) | VNTNRWFITLINQKQVKAVIGDFKLCEKAGEFDP---KKYAEFQAAIGSGEKKKTEKAPK |
| | | .*:* : :. ::  . . * * * ...:**:*.. ::.:. |
| GTT1_MOUSE | (SEQ ID NO 29) | KVKDCPPADLIIKQKLMPRVLTMIQ---------------------------------- |
| GTT1_RAT | (SEQ ID NO 30) | KVRDCPPADPVIKQKLMPRVLTMIQ---------------------------------- |
| EF1G_ARTSA | (SEQ ID NO 31) | AVKAKPEKKEVPKKEQEEPADAAEEALAAEPKSKDPFDEMPKGTFNMDDFKRFYSNNEET |
| | | *: * . : *:: . : : |
| GTT1_MOUSE | (SEQ ID NO 32) | ------------------------------------------------------------ |
| GTT1_RAT | (SEQ ID NO 33) | ------------------------------------------------------------ |
| EF1G_ARTSA | (SEQ ID NO 34) | KSIPYFWEKFDKENYSIWYSEYKYQDELAKVYMSCNLITGMFQRIEKMRKQAFASVCVFG |

TABLE 2-continued

| | | |
|---|---|---|
| GTT1_MOUSE | (SEQ ID NO 35) | ---------------------------------------------------------------- |
| GTT1_RAT | (SEQ ID NO 36) | ---------------------------------------------------------------- |
| EF1G_ARTSA | (SEQ ID NO 37) | EDNDSSISGIWVWRGQDLAFKLSPDWQIDYESYDWKKLDPDAQETKDLVTQYFTWTGTDK |
| GTT1_MOUSE | (SEQ ID NO 38) | ------------ |
| GTT1_RAT | (SEQ ID NO 39) | ------------ |
| EF1G_ARTSA | (SEQ ID NO 40) | QGRKFNQGKIFK |

TABLE 3

| | | |
|---|---|---|
| EF1G_CAEEL (100-243) | (SEQ ID NO 41) | ----NFD---KKTVEQYK--NELNGQLQVLDRVLVKKTYLVGERLSLADVSVALDLLPAF |
| SYEP_HUMAN (1-180) | (SEQ ID NO 42) | MEHTEIDHWLEFSATKLSSCDSFTSTINELNHCLSLRTYLVGNSLSLADLCVWATLKGNA |
| | | ::*    : :. :  .   :.:..  ::  *::  *  :*****:  *****:.*    * |
| EF1G_CAEEL (100-243) | (SEQ ID NO 43) | QYVLDANARKSIVNVTRWFRTVVNQPAVKEV--LGEVSLASS-VA-QFNQ--AKFTELS- |
| SYEP_HUMAN (1-180) | (SEQ ID NO 44) | AWQEQLKQKKAPVHVKRWFGFLEAQQAFQSVGTKWDVSTTKARVAPEKKQDVGKFVELPG |
| | | :    :  :  :*:  *:*.***   :  *  *.:.*        :  :.:    :  :*    ... |
| EF1G_CAEEL (100-243) | (SEQ ID NO 45) | ---AKVAKSAPKAEKPKKEAKPAAAA--AQP-----E-------DD-EPKEEKS-KDP-- |
| SYEP_HUMAN (1-180) | (SEQ ID NO 46) | AEMGKVTVRFPPEASGYLHIGHAKAALLNQHYQVNFKGKLIMRFDDTNPEKEKEDFEKVI |
| | | .**:    *    .    . * **   *       :          ** :*::**. : |

TABLE 4

| | | |
|---|---|---|
| EF1G_RABIT | (SEQ ID NO 47) | MAAGTLYTYPENWRAFKALIAAQYSGAQVRVLSAPPHFHFGQTNRTPEFLRKFPAGKVPA |
| GTH4_MAIZE | (SEQ ID NO 48) | -ATPAVKVYGWAISPFVSRALLALEEAGVDYELVPMSRQDGD-HRRPEHLARNPFGKVPV |
| | | *: ::  .*    .* :       . * *    .*   : *: :* **.* : * ****. |
| EF1G_RABIT | (SEQ ID NO 49) | FEGDDGFCVFESNAIAYYVS----NEELRGSTPEAAAQVVQWVSFADSDIVPPAST---- |
| GTH4_MAIZE | (SEQ ID NO 50) | LE-DGDLTLFESRAIARHVLRKHKPELLGGGRLEQTAMVDVWLEVEAHQLSPPAIAIVVE |
| | | :* *..: :**.*  :*       * * *. * :* *  *:..    ::  *** : |
| EF1G_RABIT | (SEQ ID NO 51) | WVFPTLGIMHHNKQATENAKEEVKRILGLLDAHLKTRTFLVGERVTLADITVVCTLLWLY |
| GTH4_MAIZE | (SEQ ID NO 52) | CVFAPFLGRERNQAVVDENVEKLKKVLEVYEARLATCTYLAGDFLSLADLSPF-TIMHCL |
| | | **..:   .:*:  ...::   *::*::*  :  :*:* *  *:*.*:   ::****:: .  *:: |
| EF1G_RABIT | (SEQ ID NO 53) | KQVLEPSFRQAFPNTNRWFLTCINQPQFRAVLGEVKLCEKMAQFDAKKFAESQPKKDTPR |
| GTH4_MAIZE | (SEQ ID NO 54) | MATEYAALVHALPHVSAWWQGLAARP---AAN-------KVAQF--MPVGAGAPKEQE-- |
| | |  .  .::  :*:*:.. *:      :*    *.          *:***   ... . **:: |

The Second Example

G Protein-Coupled Receptors

The family of G protein-coupled receptors has a long evolutionary history and is of particular importance for signal transduction in all eukaryotes. Spanning the lipid bilayer of the plasma membrane with seven helices, they bind and form signal transducing couples that are at the center of many key processes such as visual excitation, olfaction, histamine secretion in allergic reactions, and chemotaxis. G protein-coupled receptors form a very diverse family and extensive studies have shown that single descriptor approaches do not suffice to characterize the family's members.

Despite considerable efforts, very few membrane proteins have yielded high-resolution X-ray crystallographic data; this led to increased use of electron microscope approaches. The first such data were in fact obtained for bacteriorhodopsin, the bacterial analogue of rhodopsin, where a 3 Å electron-microscopy reconstruction of it has established directly the presence of the seven transmembrane helices. The significant sequence similarity that the members of this family exhibit indicates that they ought to have the same topology.

In order to demonstrate the power of the present invention and its ability to generalize, the experiment began with the contents of the GPCRDB as they existed in May 1998. Note that from this collection the hypothetical proteins from *Caenorhabditis elegans* are excluded since it was intended to carry out GPCR-discovery in this genome. The bacterial analogues of rhodopsin as well as all listed G-proteins were also excluded. What was left was a total of 1,019 GPCR entries, of which 862 were complete sequences and 157 were fragments. This set was intersected with an older release of Swiss-Prot (Release 35.0 from November 1997)

and determined that the intersection of the two databases comprised a total of 804 sequences and fragments. Starting with data that were almost two years old was intentional since it was important that the ability of the composite descriptors to generalize and identify additional candidate sequences in the much larger databases of today would be shown.

The collection of 804 GPCR sequences and fragments contained several classes (e.g. rhodopsin-like, secretin-like, pheromone, etc.) of proteins. In turn, each of these classes comprised several representatives. Instead of selecting representatives from each of the identified classes, the order of the sequences in this set of 804 members were randomized. Note that the contents of the sequences themselves remained unchanged, only their order of appearance was modified. For example, the 613-th sequence was now listed 4-th, the 11-th sequence now appeared in the 45-th position, and so on. Subsequently, a training set T was formed by collecting the sequences and fragments listed in the first 80 positions, arguably a very small set if one considers the diversity of the GPCR family. Essentially, slightly less than 1/10-th of the available dataset were randomly sub-selected for the purposes of building the composite descriptor. Table 5 below contains a listing of the labels of the 80 sequences in this training set. Table 5 shows the Swiss-Prot labels of the 80 sequences in the training set for the G protein-coupled receptor experiment. The labels are listed in the order they were selected and they correspond to both sequences and sequence fragments.

mated log-probability was equal to −30.0 or less were selected and this generated a composite descriptor that comprised 1,703 patterns.

Figure 3:
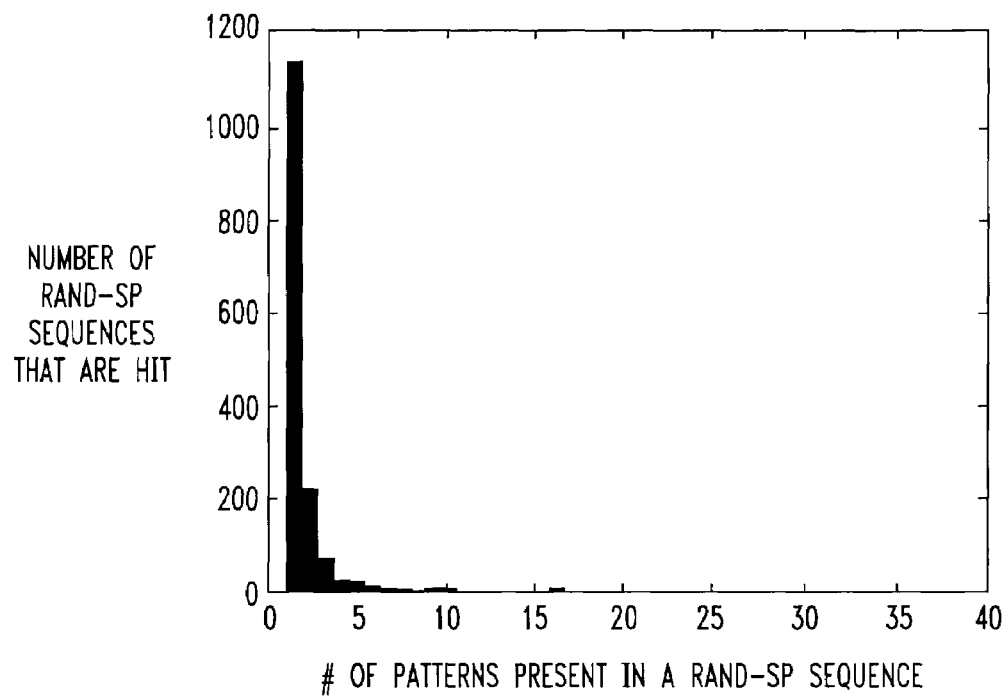
FIG. 3 is a histogram of the scores for the sequences of RAND-SP when processed by the composite descriptor for an 80-sequence G protein-coupled receptor training set.

First, the corresponding DFA (deterministic finite automaton, which will only recognize instances of the composite descriptor patterns in a query sequence and which performs method step 260) was used to search a randomized version RAND-Swiss-Prot of Swiss-Prot (Release 38.0) (see also relevant discussion in the PS50040 example). The sequence regions with non-zero local counters were identified and the maximum counter values from each such region were summed up; the sum-total was attached to the sequence label and the sequences were sorted in order of decreasing sum value. A total of 1,564 sequence fragments from RAND-Swiss-Prot received non-zero support and the actual histogram of these values is shown in FIG. 3. Of those 1,564 fragments, 1,548 received a support value that was less than 9. Thus $Thres_{rand}=10$ was selected; this threshold choice corresponded to the 99-th percentile.

Subsequently, the same DFA was used to search the actual Swiss-Prot database testing each of its 80,236 sequences for membership in the G protein-coupled receptor family. Sum values were attached to each sequence as above and only 947 sequences from Swiss-Prot that received support greater than or equal to $Thres_{rand}=10$ were kept.

In order to determine the quality of the composite descriptor and determine the number of true and false positives that the descriptor gives rise to, the Swiss-Prot annotation (keyword "KW" lines) was used for each of these 947 sequences.

TABLE 5

| 1 through 20 | 21 through 40 | 41 through 60 | 61 through 80 |
|---|---|---|---|
| EBI2_HUMAN | OPSD_CORAU | ACM2_HUMAN | PACR_RAT |
| ML1X_HUMAN | ACM4_XENLA | VIPR_MELGA | CRFR_CHICK |
| ACM3_CHICK | G10D_MOUSE | V1BR_HUMAN | OLF9_RAT |
| P2YR_MOUSE | OLF4_CHICK | MGR8_HUMAN | ACM4_MOUSE |
| OAR_DROME | ACM3_PIG | SSR4_RAT | NY4R_MOUSE |
| AA1R_CHICK | 5H1A_MOUSE | HH1R_MOUSE | 5HTB_DROME |
| MAM2_SCHPO | MSHR_BOVIN | NK2R_RAT | GU38_RAT |
| SCRC_RAT | OLF5_RAT | MSHR_HUMAN | PF2R_BOVIN |
| PAFR_CAVPO | GU03_RAT | A2AA_PIG | OPSB_GECGE |
| ACM3_RAT | P2YR_BOVIN | B3AR_BOVIN | AA3R_HUMAN |
| OL1J_HUMAN | GPCR_LYMST | OPSB_HUMAN | MC3R_MOUSE |
| GPRJ_MOUSE | FMLR_RABIT | GPRO_HUMAN | BAR2_SCHCO |
| D4DR_MOUSE | B1AR_HUMAN | 5H2A_CRIGR | CRFR_HUMAN |
| ML1C_CHICK | D3DR_RAT | PER4_MOUSE | MC4R_RAT |
| PER2_RAT | PF2R_MOUSE | OPSD_CATBO | OPSB_ANOCA |
| OPRX_PIG | PER1_RAT | ACM1_RAT | IL8A_RAT |
| AA1R_HUMAN | GRPR_MOUSE | OPS2_SCHGR | AA1R_CAVPO |
| DOP1_DROME | GRFR_PIG | GRHR_HUMAN | AG2R_HUMAN |
| OXYR_RAT | NK1R_RANCA | NK1R_RAT | GPRM_HUMAN |
| B3AR_MOUSE | OLF1_HUMAN | EDG2_SHEEP | CASR_HUMAN |
| EBI2_HUMAN | OPSD_CORAU | ACM2_HUMAN | PACR_RAT |
| ML1X_HUMAN | ACM4_XENLA | VIPR_MELGA | CRFR_CHICK |
| ACM3_CHICK | G10D_MOUSE | V1BR_HUMAN | OLF9_RAT |
| P2YR_MOUSE | OLF4_CHICK | MGR8_HUMAN | ACM4_MOUSE |
| OAR_DROME | ACM3_PIG | SSR4_RAT | NY4R_MOUSE |

As in the previous example, the patterns were discovered assuming the equivalence classes {A, G}, C, {D, E}, {F, Y}, H, {I, L, M, V}, {K, R}, {N, Q}, P, {S, T}, W. The Teiresias parameters were set to L=5, W=10, whereas the successive threshold choices were K=80, K=16 and K=3. It was set out to discover patterns that involved at least 5 non-wild cards in any rolling window that spans 10 positions and begins/ends with a literal, which is a relatively high-degree of local similarity (i.e., 50% or higher). Those patterns whose estimated log-probability was Of these retrieved sequences, 928 are actually listed as 'G protein-coupled receptor's, 10 are eukaryotic transmembrane proteins (SUR7_YEAST, C561_HUMAN, YIPC_YEAST, NU4M_APIME, SCG2_XENLA, GTR2_LEIDO, GARP_HUMAN, CIN6_HUMAN, CIN3_RAT, PLSC_COCNU), 2 are hypothetical eukaryotic transmembrane proteins (YJZ3_YEAST, YMJC_CAEEL), 2 are hypothetical proteins (YKY4_YEAST, YCX7_YEAST), and finally 5 are bacterial false positives (PIP_BACCO, VIRR_AGRT6, YQGP_BACSU, HBD_CLOTS, PROA_HAEIN).

This is a very notable result, given the comparatively small amount of information that is captured by the 80-sequence input set and the diversity of the G protein-coupled receptor family. Table 6 below contains a listing of the labels of the 947 Swiss-Prot sequences whose support exceeded threshold; the labels are listed in order of decreasing value of the global counter that was associated with the corresponding sequence, and the 5 false positives are shown in boldface. Table 6 shows the labels of the 947 sequences from Swiss-Prot Release 38.0 that received support above threshold in the G protein-couple receptor example. The 5 false positives are shown with an "(FP)."

TABLE 6

| 1 through 50 | 51 through 100 | 101 through 150 | 151 through 200 | 201 through 250 |
|---|---|---|---|---|
| OAR_DROME | B2AR_CANFA | A2AC_DIDMA | 5H1A_RAT | MSHR_CEREL |
| B3AR_MOUSE | AA1R_RAT | ACM4_XENLA | 5H1A_MOUSE | MSHR_CAPHI |
| B3AR_CAVPO | AA1R_RABIT | ACM1_MOUSE | 5H1A_HUMAN | MSHR_CAPCA |
| B3AR_RAT | AA1R_HUMAN | AA3R_SHEEP | SCRC_RABIT | MSHR_ALCAA |
| OAR_HELVI | AA1R_CANFA | AA2B_CHICK | A1AA_CANFA | VIPR_CARAU |
| OAR_BOMMO | AA1R_CHICK | ACM4_MOUSE | MC5R_HUMAN | VIPR_HUMAN |
| OAR2_LOCMI | B1AR_XENLA | ACM4_HUMAN | AA3R_CANFA | HH1R_BOVIN |
| OAR1_LOCMI | NK1R_RANCA | 5H4_CAVPO | 5H4_RAT | 5HT_LYMST |
| GREC_BALAM | B1AR_SHEEP | AA2B_HUMAN | NK2R_CAVPO | HH1R_RAT |
| B1AR_RAT | AA1R_BOVIN | NK1R_RAT | SSR1_RAT | HH1R_HUMAN |
| B1AR_MOUSE | A2AA_CAVPO | NK1R_MOUSE | SSR1_MOUSE | HH1R_CAVPO |
| B1AR_PIG | A2AA_HUMAN | MC5R_RAT | SSR1_HUMAN | SSR3_HUMAN |
| B1AR_MACMU | 5H2B_HUMAN | MC5R_MOUSE | NK4R_HUMAN | 5HT_BOMMO |
| B1AR_HUMAN | AA1R_CAVPO | MC5R_BOVIN | OPRK_RAT | NK2R_HUMAN |
| B1AR_CANFA | ACM3_PIG | MC5R_SHEEP | OPRK_MOUSE | NK3R_RAT |
| B1AR_MELGA | ACM3_HUMAN | AA3R_RAT | OPRK_HUMAN | NK3R_MOUSE |
| B4AR_MELGA | ACM3_CHICK | DOP1_DROME | OPRK_CAVPO | NK3R_HUMAN |
| B3AR_BOVIN | ACM3_BOVIN | AA2B_RAT | 5HTA_DROME | SSR3_RAT |
| B3AR_CANFA | A2AC_HUMAN | AA2B_MOUSE | AA3R_RABIT | SSR3_MOUSE |
| PACR_RAT | 5H7_RAT | A1AB_RAT | A2AB_RABIT | MSHR_MOUSE |
| B3AR_MACMU | 5H7_MOUSE | A1AB_MOUSE | A2AB_MACPR | GRFR_PIG |
| B3AR_HUMAN | 5H7_HUMAN | A1AB_MESAU | MC3R_MOUSE | NK2R_RABIT |
| B2AR_MOUSE | 5H7_CAVPO | A1AB_HUMAN | MC3R_HUMAN | NK2R_BOVIN |
| SCRC_RAT | A2AD_HUMAN | D3DR_HUMAN | 5H1B_FUGRU | VIPR_PIG |
| B2AR_RAT | A2AC_RAT | D3DR_CERAE | ACM4_RAT | 5H1A_FUGRU |
| B2AR_MESAU | A2AC_MOUSE | NK1R_HUMAN | A2AB_TALEU | 5HTB_DROME |
| B2AR_BOVIN | A2AC_CAVPO | NK1R_CAVPO | A2AB_PROHA | VIPS_HUMAN |
| B2AR_PIG | VIPR_RAT | SSR4_RAT | A2AB_ORYAF | MC4R_RAT |
| 5H2A_PIG | A2AA_RAT | SSR4_MOUSE | A2AB_HORSE | MC4R_HUMAN |
| 5H2A_MACMU | A2AA_PIG | SSR4_HUMAN | A2AB_ERIEU | A1AB_CANFA |
| 5H2A_HUMAN | A2AA_MOUSE | D2D1_XENLA | A2AB_ELEMA | NK2R_RAT |
| 5H2A_CRIGR | ACM3_RAT | AA3R_HUMAN | A2AB_DUGDU | NK2R_MOUSE |
| 5H2A_RAT | A2AR_LABOS | 5H7_XENLA | A1AD_HUMAN | NK2R_MESAU |
| 5H2A_MOUSE | ACM4_CHICK | D3DR_RAT | A2AB_DIDMA | D2D2_XENLA |
| PACR_MOUSE | AA2A_HUMAN | D3DR_MOUSE | A1AD_RAT | MSHR_HUMAN |
| 5H2C_RAT | AA2A_CANFA | A1AA_ORYLA | A1AD_RABIT | 5H1F_RAT |
| 5H2C_HUMAN | AA2A_RAT | A2AB_CAVPO | A1AD_MOUSE | 5H1F_MOUSE |
| 5H2C_MOUSE | AA2A_MOUSE | D2DR_MOUSE | OPRM_RAT | 5H1F_CAVPO |
| PACR_BOVIN | A1AA_RAT | D2DR_HUMAN | OPRM_PIG | 5H1F_HUMAN |
| 5H2B_MOUSE | A1AA_RABIT | D2DR_FUGRU | OPRM_MOUSE | DOP2_DROME |
| PACR_HUMAN | A1AA_HUMAN | D2DR_CERAE | OPRM_HUMAN | HH2R_CAVPO |
| D4DR_RAT | A1AA_BOVIN | D2DR_BOVIN | OPRM_BOVIN | HH2R_CANFA |
| D4DR_MOUSE | ACM2_RAT | A2AB_RAT | MC3R_RAT | HH1R_MOUSE |
| SCRC_HUMAN | ACM2_PIG | A2AB_MOUSE | AA2A_CAVPO | GASR_PRANA |
| D4DR_HUMAN | ACM2_HUMAN | A2AB_HUMAN | MSHR_BOVIN | GASR_HUMAN |
| VIPR_MELGA | ACM2_CHICK | 5H4_MOUSE | MSHR_VULVU | A2AB_BOVIN |
| 5H2B_RAT | ACM5_RAT | ACM1_RAT | MSHR_SHEEP | 5H1B_RABIT |
| A2AR_CARAU | ACM5_MACMU | ACM1_PIG | MSHR_RANTA | MSHR_HORSE |
| B2AR_MACMU | ACM5_HUMAN | ACM1_MACMU | MSHR_OVIMO | GASR_RABIT |
| B2AR_HUMAN | 5HT1_DROME | ACM1_HUMAN | MSHR_DAMDA | GASR_MOUSE |
| 251 through 300 | 301 through 350 | 351 through 400 | 401 through 450 | 451 though 500 |
| GASR_CANFA | IL8B_GORGO | GPRL_HUMAN | AG2T_RAT | BRS4_BOMOR |
| GASR_BOVIN | IL8B_BOVIN | MGR8_HUMAN | ML1A_SHEEP | V1BR_RAT |
| 5H1D_RAT | 5H5A_RAT | GPCR_LYMST | ML1A_PHOSU | BRS3_SHEEP |
| 5H1D_MOUSE | 5H5A_MOUSE | A2AB_AMBHO | ML1A_HUMAN | BRS3_MOUSE |
| 5H1D_FUGRU | 5H6_HUMAN | BRB2_HUMAN | MGR8_RAT | BRS3_HUMAN |
| 5H1D_CAVPO | VIPS_RAT | OLF5_RAT | IL8A_GORGO | OPSG_CHICK |
| 5H1B_SPAEH | VIPS_MOUSE | 5H1E_HUMAN | GRPR_HUMAN | MGR8_MOUSE |
| 5H1B_RAT | VIPR_MOUSE | 5H1D_RABIT | GPRC_RAT | OPSB_ANOCA |
| 5H1B_MOUSE | CCKR_RAT | OPS1_PATYE | GPRC_MOUSE | GHSR_RAT |
| GASR_RAT | CCKR_HUMAN | CKR1_MACMU | GPRC_HUMAN | GHSR_PIG |
| YYI3_CAEEL | CCKR_CAVPO | CKR1_HUMAN | GPR3_MOUSE | GHSR_HUMAN |
| MSHR_CHICK | IL8B_PANTR | BRB2_MOUSE | GPR3_HUMAN | FML1_PANTR |
| 5H1B_CRIGR | IL8B_MACMU | DADR_XENLA | EDG2_SHEEP | SSRL_FUGRU |
| 5H1B_CAVPO | IL8B_HUMAN | DADR_PIG | EDG2_MOUSE | CASR_RAT |

TABLE 6-continued

| | | | | |
|---|---|---|---|---|
| SSR2_RAT | IL8A_PANTR | DADR_HUMAN | EDG2_HUMAN | 5HT2_APLCA |
| SSR2_MOUSE | IL8A_HUMAN | DADR_DIDMA | BLR1_MOUSE | OPSD_ALLMI |
| B3AR_PIG | AG2R_MELGA | D1DR_CARAU | OLF4_RAT | CCR4_RAT |
| SSR2_HUMAN | AG2R_CHICK | 5HT1_APLCA | GRPR_RAT | CCR4_PAPAN |
| 5H1B_HUMAN | OLF0_RAT | 5H2A_CANFA | GRPR_MOUSE | CCR4_MOUSE |
| OPRX_RAT | GPRF_HUMAN | OLF9_RAT | GALS_HUMAN | CCR4_MACMU |
| OPRX_MOUSE | CCKR_XENLA | OLF1_RAT | FMLR_MACMU | CCR4_MACFA |
| OPRX_CAVPO | AG2S_RAT | FML1_PONPY | CKR3_MACMU | CCR4_HUMAN |
| HH2R_HUMAN | AG2S_MOUSE | DCDR_XENLA | AG2R_RABIT | CCR4_FELCA |
| 5H1D_HUMAN | AG2S_HUMAN | DADR_RAT | EDG2_BOVIN | CCR4_CERTO |
| 5H1D_CANFA | AG2R_RAT | FML1_MACMU | GALS_RAT | CCR4_BOVIN |
| HH2R_RAT | AG2R_PIG | FML1_HUMAN | GALS_MOUSE | APJ_HUMAN |
| OPRX_PIG | AG2R_MOUSE | FML1_GORGO | G10D_RAT | OPSD_RANTE |
| OPRX_HUMAN | AG2R_MERUN | GPR1_RAT | G10D_MOUSE | 5H1B_PIG |
| SSR2_PIG | AG2R_HUMAN | BRB2_RAT | OPSD_RAT | CKR8_MOUSE |
| SSR2_BOVIN | AG2R_CANFA | GALR_RAT | CKR3_MOUSE | CKR1_MOUSE |
| TLR2_DROME | AG2R_BOVIN | GALR_MOUSE | V1BR_HUMAN | OPSP_CHICK |
| HH2R_MOUSE | 5H6_RAT | GALR_HUMAN | FML1_MOUSE | OPSD_OCTDO |
| 5H1B_DIDMA | GPRF_MACNE | D5DR_FUGRU | OPSD_CRIGR | OPRM_CAVPO |
| A2AB_ECHTE | GPRF_CERAE | D1DR_OREMO | BRS3_CAVPO | OPSX_MOUSE |
| 5HT_HELVI | GP38_HUMAN | FMLR_MOUSE | ML1A_CHICK | OPSX_HUMAN |
| 5H1D_PIG | 5H2A_CAVPO | BRB2_RABIT | TLR1_DROME | C3AR_HUMAN |
| OPRD_RAT | CCKR_MOUSE | SSR5_HUMAN | OPSD_TRIMA | OPSD_RAJER |
| OPRD_MOUSE | YDBM_CAEEL | DBDR_RAT | OPSD_SHEEP | ML1X_HUMAN |
| OPRD_HUMAN | NYR_DROME | DBDR_HUMAN | OPSD_RABIT | AG2S_XENLA |
| GALT_RAT | OLFD_CANFA | 5H2B_PIG | OPSD_PIG | OLF6_RAT |
| GALT_MOUSE | GRFR_MOUSE | ML1A_MOUSE | OPSD_PHOVI | ML1B_HUMAN |
| 5HSA_HUMAN | GRFR_HUMAN | MC4R_MOUSE | OPSD_PHOGR | OLFJ_HUMAN |
| GPRA_HUMAN | SSR5_RAT | MAM2_SCHPO | OPSD_PETMA | ML1B_CHICK |
| IL8B_RAT | SSR5_MOUSE | FMLR_RABIT | OPSD_MOUSE | GPRJ_HUMAN |
| IL8B_MOUSE | OLFE_HUMAN | D1DR_FUGRU | OPSD_MACPA | GPR4_PIG |
| IL8A_RABIT | OPRD_PIG | IL8A_RAT | OPSD_HUMAN | GPR4_HUMAN |
| GRFR_RAT | IL8B_RABIT | BLR1_RAT | OPSD_CANFA | CKR8_HUMAN |
| 5H5B_RAT | OLF4_CANFA | DBDR_XENLA | OPSD_BOVIN | GPRJ_MOUSE |
| 5H5B_MOUSE | GU27_RAT | CASR_HUMAN | GALT_HUMAN | GPR8_HUMAN |
| GPRA_RAT | OLFI_HUMAN | BLR1_HUMAN | OAR2_LYMST | OPSD_XENLA |

| 501 through 550 | 551 through 600 | 601 through 650 | 651 through 700 | 701 though 750 |
|---|---|---|---|---|
| OPSD_TURTR | NY2R_PIG | OPSI_ASTFA | GC96_HUMAN | OPSP_PETMA |
| OPSD_RANPI | NY2R_HUMAN | OPSG_ORYLA | YTJ5_CAEEL | OPSD_ZEUFA |
| OPSD_RANCA | NY2R_BOVIN | OPSG_CARAU | OLF8_RAT | OPSD_COTBO |
| OPSD_MESBI | NY2R_MOUSE | OPSD_GAMAF | NY1R_XENLA | OPSD_ABYKO |
| OPSD_GLOME | CKR6_HUMAN | FML2_MACMU | GPR5_HUMAN | OLF2_CHICK |
| OPSD_DELDE | C3AR_MOUSE | C5AR_CANFA | GIPR_RAT | DADR_BOVIN |
| OPSD_BUFMA | VQ3L_CAPVK | TRFR_CHICK | C5AR_RAT | OLF5_CHICK |
| OPSD_BUFBU | OXYR_PIG | THRR_RAT | BONZ_HUMAN | OLF3_CHICK |
| OPSD_AMBTI | OXYR_MOUSE | THRR_PAPHA | YR42_CAEEL | OLF1_CHICK |
| ML1C_CHICK | OXYR_MACMU | THRR_MOUSE | OPSD_NEOAU | FSHR_PIG |
| CASR_BOVIN | OXYR_BOVIN | THRR_HUMAN | CKR4_HUMAN | FSHR_MACPA |
| TRFR_SHEEP | EDG1_RAT | THRR_CRILO | V1AR_HUMAN | FSHR_HUMAN |
| TRFR_RAT | EDG1_MOUSE | CCR3_HUMAN | OPSD_SARTI | FSHR_HORSE |
| TRFR_MOUSE | EDG1_HUMAN | GPRO_RAT | OPSD_SARSP | FSHR_EQUAS |
| TRFR_HUMAN | ACTR_HUMAN | THRR_XENLA | BONZ_MACNE | DBDR_BOVIN |
| OXYR_HUMAN | OPSD_SARPU | PTRR_DIDMA | BONZ_CERAE | AG22_SHEEP |
| OPSD_LAMJA | DADR_RABIT | NTR1_HUMAN | RDC1_HUMAN | US28_HCMVA |
| OPSD_CHICK | C5AR_GORGO | 5H1E_PIG | PTRR_PIG | PTRR_RAT |
| ML1C_XENLA | YLD1_CAEEL | OLF3_CANFA | PTRR_HUMAN | PTRR_MOUSE |
| GPRX_ORYLA | FMLR_PONPY | GPRJ_RAT | YR13_CAEEL | OPSB_APIME |
| OPS1_SCHGR | OPSB_CONCO | GPRD_HUMAN | OPSD_NEOSA | OLF7_RAT |
| OLF2_RAT | ML1X_MOUSE | GIPR_HUMAN | OPSD_COMDY | OL1C_HUMAN |
| ML1X_SHEEP | FSHR_SHEEP | OPSF_ANGAN | OPSD_CATBO | NY6R_MOUSE |
| CCR4_SHEEP | FSHR_BOVIN | OPSD_TAUBU | OLF6_MOUSE | ET1R_RAT |
| PE22_RAT | ACTR_BOVIN | OPSD_BATNI | OPSD_CAMAB | ET1R_PIG |
| OPSP_COLLI | PE22_MOUSE | OPSD_BATMU | OLF1_HUMAN | ET1R_HUMAN |
| GPR6_RAT | PE22_HUMAN | P2Y9_HUMAN | OLF1_CANFA | ET1R_BOVIN |
| GPR6_HUMAN | OX2R_RAT | P2Y5_HUMAN | ETBR_RAT | OPSB_CHICK |
| ACM1_DROME | OX2R_HUMAN | P2Y5_CHICK | ETBR_PIG | OLF2_HUMAN |
| V1AR_MOUSE | 5H1B_CANFA | OXYR_SHEEP | ETBR_MOUSE | OPSD_LIMPA |
| FMLR_PANTR | OGR1_HUMAN | OPSD_NEOAR | ETBR_HUMAN | OPSD_CYPCA |
| FMLR_HUMAN | GPRV_HUMAN | NMBR_RAT | ETBR_HORSE | OPSD_CARAU |
| RDC1_CANFA | ACTR_MOUSE | NMBR_MOUSE | ETBR_COTJA | OL15_MOUSE |
| OPSD_ANOCA | ACTR_MESAU | TDA8_MOUSE | ETBR_CANFA | GU58_RAT |
| GPRK_HUMAN | FMLR_GORGO | H218_RAT | ETBR_BOVIN | GU38_RAT |
| FML2_PONPY | OPSB_GECGE | GPRH_HUMAN | OPS2_LIMPO | GU01_RAT |
| FML2_PANTR | RDC1_MOUSE | CKR7_MOUSE | OPS1_LIMPO | OPSD_PARKN |
| FML2_HUMAN | OXYR_RAT | CKR7_HUMAN | OL7B_MOUSE | OPSD_COTIN |
| FML2_GORGO | OPSU_BRARE | AG22_RAT | OL1D_HUMAN | NY6R_RABIT |
| EBI2_HUMAN | OPSD_SARXA | AG22_MOUSE | OL1A_HUMAN | OPSD_ICTPU |

TABLE 6-continued

| | | | | |
|---|---|---|---|---|
| C5AR_PONPY | OPSD_SARMI | AG22_HUMAN | GU03_RAT | GPRD_RAT |
| C5AR_PANTR | OPSD_SARDI | OLF3_HUMAN | GRHR_CLAGA | GIPR_MESAU |
| C5AR_HUMAN | OPSD_MYRBE | CKR4_MOUSE | CKR3_HUMAN | OPSB_ASTFA |
| V1AR_SHEEP | NTR1_RAT | OPSD_ANGAN | CKR3_CERAE | GU45_RAT |
| V1AR_RAT | GPRO_HUMAN | NMBR_HUMAN | C5AR_MACMU | DEZ_HUMAN |
| OPSP_ICTPU | OPSH_CARAU | OPSD_TODPA | YWO1_CAEEL | OL13_MOUSE |
| NY2R_CAVPO | OPSD_POERE | OPSD_SEPOF | OL1G_HUMAN | GPR7_HUMAN |
| GPR1_HUMAN | OPSD_ORYLA | OPSD_PROJE | YT66_CAEEL | OX1R_RAT |
| AG2R_XENLA | OPSD_MYRVI | OPSD_LOLFO | OLF4_CHICK | OX1R_HUMAN |
| OLF3_RAT | C5AR_MOUSE | OPSD_COTGR | HM74_HUMAN | BRB1_RABIT |

| 751 through 800 | 801 through 850 | 851 through 900 | 901 through 947 |
|---|---|---|---|
| YPHD_ECOLI | US27_HCMVA | GRHR_MOUSE | P2YR_MOUSE |
| OPSD_SPHSP | NODC_RHISM | GRHR_HUMAN | P2YR_HUMAN |
| OPSD_LOLSU | GP42_HUMAN | GRHR_HORSE | P2YR_BOVIN |
| GPRP_HUMAN | GP41_HUMAN | GRHR_BOVIN | OPSB_ORYLA |
| CKRV_MOUSE | MGR4_RAT | GPR2_HUMAN | NU4M_APIME |
| CKR5_RAT | LSHR_SHEEP | GLPR_MOUSE | ML1A_BOVIN |
| CKR5_MOUSE | LSHR_PIG | GLPR_HUMAN | YCX7_YEAST |
| BAR2_SCHCO | LSHR_HUMAN | FSHR_RAT | SCG2_XENLA |
| PI2R_HUMAN | LSHR_CALJA | YKY4_YEAST | PIP_BACCO (FP) |
| OPSD_COTKE | GLR_MOUSE | OX2R_PIG | PI2R_RAT |
| VK02_SPVKA | EDGL_MOUSE | OPSV_CHICK | PI2R_BOVIN |
| DEZ_RAT | OPSD_POMMI | OPSB_SAIBB | PAFR_RAT |
| DEZ_MOUSE | MGR7_RAT | OPSB_RAT | P2UR_RAT |
| CKR5_PAPHA | MGR7_HUMAN | OPSB_MOUSE | P2UR_MOUSE |
| CKR5_PANTR | CML2_RAT | OPSB_HUMAN | P2UR_HUMAN |
| CKR5_MACMU | NY1R_RAT | OPS4_DROPS | OPSR_ORYLA |
| CKR5_GORGO | NY1R_PIG | OL1L_HUMAN | OPSO_SALSA |
| CKR5_CERTO | NY1R_MOUSE | OL1B_HUMAN | GTR2_LEIDO |
| CKR5_CERAE | NY1R_HUMAN | HBD_CLOTS (FP) | GLHR_ANTEL |
| CKR2_MOUSE | NY1R_CANFA | GRHR_RAT | GARP_HUMAN |
| CKR2_HUMAN | RTA_RAT | EDG3_HUMAN | PAFR_MOUSE |
| OPSB_CARAU | OPSV_XENLA | C561_HUMAN | OPSD_APIME |
| OPS2_PATYE | OPSU_CARAU | YIPC_YEAST | MAS_RAT |
| GP43_HUMAN | OPS1_DROPS | PTH2_RAT | MAS_MOUSE |
| GCRC_MOUSE | OPS1_DROME | PAFR_CAVPO | MAS_HUMAN |
| BRB1_HUMAN | OPS1_CALVI | OPSB_BOVIN | CIN6_HUMAN |
| VC03_SPVKA | MGR6_RAT | OPS2_SCHOR | CIN3_RAT |
| PE24_RAT | GLPR_RAT | OLF6_CHICK | CB1R_RAT |
| PE24_RABIT | ETBR_MACFA | NY4R_RAT | CB1R_MOUSE |
| PE24_MOUSE | TSHR_SHEEP | NY4R_MOUSE | CB1R_HUMAN |
| PE24_HUMAN | TSHR_BOVIN | GRHR_PIG | CB1R_FELCA |
| YYO1_CAEEL | OPSR_HORSE | GPRM_HUMAN | CB1B_FUGRU |
| YR41_CAEEL | OPSG_ODOVI | GP39_HUMAN | CB1A_FUGRU |
| V2R_RAT | LSHR_RAT | PTR2_HUMAN | YQGP_BACSU(FP) |
| V24_PIG | LSHR_MOUSE | PE21_RAT | VIRR_AGRT6(FP) |
| V2R_HUMAN | LSHR_BOVIN | PE21_MOUSE | PLSC_COCNU |
| V2R_BOVIN | GLR_RAT | PAFR_HUMAN | OPS6_DROME |
| OPS1_HEMSA | DBDR_MACMU | OPS4_DROME | NY5R_RAT |
| CML2_HUMAN | TSHR_MOUSE | GLR_HUMAN | NY5R_PIG |
| CKR5_HUMAN | TSHR_HUMAN | YMJC_CAEEL | NY5R_MOUSE |
| P2Y7_HUMAN | TSHR_CANFA | PE21_HUMAN | NY5R_HUMAN |
| OPSH_ASTFA | SUR7_YEAST | OPSD_CORAU | NY5R_CANFA |
| OPSG_ASTFA | OPSG_GECGE | OL1H_HUMAN | NTR2_RAT |
| OPSD_ASTFA | OLF2_CANFA | YJZ3_YEAST | NTR2_MOUSE |
| OPS5_DROME | MGR6_HUMAN | PROA_HAEIN(FP) | MGR3_RAT |
| MGR4_HUMAN | GPRI_HUMAN | LSHR_CHICK | MGR3_HUMAN |
| ACTR_PAPHA | GPRE_RAT | FSHR_CHICK | GUSB_BOVIN |
| OPSD_LIMBE | NY4R_HUMAN | PI2R_MOUSE | |
| YXX5_CAEEL | ET3R_XENLA | PF2R_MOUSE | |
| AA1R_MOUSE | GRHR_SHEEP | P2YR_RAT | |

A Third Example

The Helix-Turn-Helix DNA Binding Motif

The third example that showcases the present invention corresponds to the helix-turn-helix motif that mediates the binding of many regulatory proteins to regulatory control sites of DNA. This 20 amino-acid long structural motif consists of two helices (7 and 9 a.a. respectively) that are separated by a 4 amino acid turn that are held together through non-polar interactions of their side chains. It has been argued that sequence-based analysis using traditional approaches cannot unambiguously identify helix-turn-helix motifs unless it is combined with the use of stereo-chemical constraints. More recently, a pattern-based approach started with 91 carefully-selected, aligned sequence fragments that corresponded to known helix-turn-helix instances and produced significant results by essentially estimating a pattern-based profile for the helix-turn-helix binding motif. This set of 91 fragments is particularly interesting because it is a very diverse collection of helix-turn-helix motif instances that share very little at the sequence level.

In the experiment carried out, a subset of 70 fragments from the set of 91 were selected (excluding those of the helix-turn-helix instances that corresponded to pieces of homeoboxes) and no alignment information was assumed. Additionally, each of the fragments was extended to the left and to the right by including an additional 10 amino acids, thus producing fragments that were 40 amino acids long. Again, the patterns were discovered assuming the equivalence classes {A, G}, C, {D, E}, {F, Y}, H, {I, L, M, V}, {K, R}, {N, Q}, P, {S, T}, W. The Teiresias parameters were set to L=5, W=10 whereas the successive threshold choices were K=70/5=14, K=3 and K=2. It was set out to discover patterns that involved at least 5 non-wild cards in any rolling window spanning 10 positions that begins/ends with a literal, a relatively high-degree of local similarity (i.e. 50% or higher). From the discovered set, those patterns whose estimated log-probability was equal to −30.0 or less were selected, thus giving rise to a composite descriptor with 517 patterns. Table 7 below lists the labels of the 70 fragments in this training set. Table 7 shows Swiss-Prot labels of the 70 sequence fragments with length 40 a.a. in the training set for the helix-turn-helix experiment.

Figure 4:
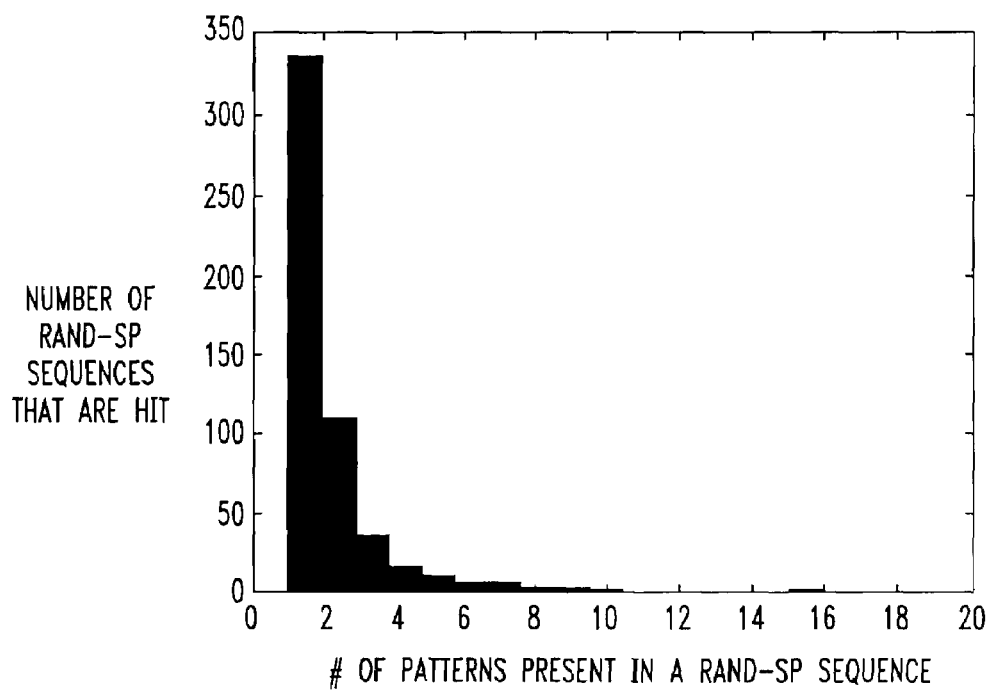
FIG. 4 is a histogram of the scores for the sequences of RAND-SP when processed by the composite descriptor for a 70-sequence helix-turn-helix training set.

RAND-Swiss-Prot of Swiss-Prot (Release 38.0) and therein were discovered a total of 277 randomized sequences that received non-zero support. Of the 277 randomized sequences, 275 received a support value that was less than or equal to 6. Thus, $Thres_{rand}$ was set equal to 7. This threshold choice corresponded to the 99.2-th percentile. FIG. 4 shows the histogram of the scores for the sequences of RAND-Swiss-Prot that received non-zero support.

Subsequent search of the actual Swiss-Prot database gave rise to 193 sequences that received support greater than or equal to $Thres_{rand}=7$. The support values ranged from the minimum allowed value of 7 to a maximum value of 66.

Next, the Swiss-Prot annotation (feature table "FT" lines and description "DE" lines) was used for each of these 193 sequences. Of these, 169 are actually listed in Swiss-Prot as containing a helix-turn-helix motif, 2 are listed as belonging to an H-T-H group from PFAM (Y4WC_RHISN, Y4AM_RHISN) and 3 are listed as having dna-binding properties (VR2B_BPT4) or being putative DNA replication proteins (Y4CK_RHISN) or being a cytosine-specific methyltransferase (MTE8_SECOLI). Of the remaining proteins, 1 is listed as hypothetical protein (YP60_METTM), 1 is listed as a hypothetical transcription factor containing a helix-turn-helix motif (Y558_METJA), 1 is listed as being involved in DNA packaging (XTMA_BACSU), 1 is listed as having strong similarity to MJ1545 which is a putative transcription repressor protein containing a helix-turn-helix motif (YO14_ARCFU), 3 have very good blastp P-values with all the similarities confined in the helix-turn-helix region of the input fragments (PRPD_SALTY, PRPD_E-COLI, Y0FO_MYCTU), and finally, 2 are likely to be false positives (YOAE_ECOLI, CTPE_MYCTU). Table 8 below contains a listing of the labels of these 193 hits in order of decreasing value of accumulated support. Table 8 shows the Swiss-Prot labels of the 193 sequence fragments that are discovered using the composite descriptor derived from the original set of 70 fragments.

TABLE 7

| 1 through 20 | 21 through 40 | 41 through 60 | 61 through 70 |
| --- | --- | --- | --- |
| BIRA_ECOLI | TNP0_ECOLI | TNP3_ECOLI | RCRO_BPP22 |
| CYTR_ECOLI | DNIV_BPP1 | DNIV_ECOLI | VG30_BPPH8 |
| RBTR_KLEAE | VPB_BPMU | DNIV_SALTY | RPC_BPPH1 |
| ASNC_ECOLI | LACI_ECOLI | RCR0_LAMBD | DBNE_BPMU |
| CRP_ECOLI | PURR_ECOLI | RPC2_LAMBD | DBNE_BPD10 |
| ARAC_ERWCH | DEOR_ECOLI | RCRO_BP434 | RP32_ECOLI |
| ADA_ECOLI | ARAC_ECOLI | RPC1_BPP22 | RPSF_BACSU |
| DICC_ECOLI | FNR_ECOLI | RPC1_BPPH8 | RPSE_BACSU |
| LYSR_ECOLI | DICA_ECOLI | RPC_BP163 | RP54_KLEPN |
| ILVY_ECOLI | FIS_ECOLI | RPC_BPP2 | RP54_AZOVI |
| TRPI_PSEAE | METR_SALTY | VPC_BPMU | |
| NOD2_RHIME | AMPR_ENTCL | RPSD_BUCAP | |
| XYLR_BACSU | NOD1_RHIME | RPSA_BACSU | |
| NIFA_RHIME | XYLS_PSEPU | RPSB_BACSU | |
| NTRC_RHIME | NIFA_KLEPN | RP54_RHIME | |
| MERR_STAAU | NTRC_KLEPN | PARB_ECOLI | |
| NAHR_PSEPU | MERR_BACSR | SOPB_ECOLI | |
| TER2_ECOLI | MERR_PSEAE | RPC1_LAMBD | |
| TNP2_ECOLI | TER3_ECOLI | RPC1_BP434 | |
| TNP1_ECOLI | TNP5_PSEAE | RPC2_BPP22 | |

The resulting DFA (deterministic finite automaton, which will only recognize instances of the composite descriptor patterns in a query sequence and which performs method step 260) was used to search the randomized version

TABLE 8

| 1 through 50 | 51 through 100 | 101 through 150 | 151 through 193 |
|---|---|---|---|
| RPSF_BACSU | RP54_CAUCR | RPSD_SERMA | NIFA_KLEOX |
| RPSE_BACSU | RBSR_ECOLI | RPSD_SALTY | MERR_BACSR |
| RPSF_BACLI | PURR_HAEIN | RPSD_PSEFL | HIPB_ECOLI |
| RP35_BACTK | FIS_HAEIN | RPSD_PSEAE | FIXK_BRAJA |
| RPSE_CLOAB | TNP2_ECOLI | RPSD_ECOLI | CTPE_MYCTU |
| RPSF_BACME | RPC1_BPP22 | RPSD_BUCAP | YCIT_ECOLI |
| RPSG_CLOAB | RP54_AZOCA | RPC1_BPD3 | RPSD_NEIGO |
| RPSB_BACSU | RP32_PROMI | RP55_BRAJA | RPOD_STRPN |
| RPC1_LAMBD | RP32_ENTCL | RP54_RHISN | RPC_BPPH1 |
| RPSG_BACSU | RP32_ECOLI | RP54_RHILP | REGL_STRLI |
| TER3_ECOLI | RP32_CITFR | RP32_SERMA | PRPD_SALTY |
| VG30_BPPH8 | NTRC_BRASR | PURR_ECOLI | PRPD_ECOLI |
| LACI_ECOLI | NTRC_AZOCA | NTRC_RHOCA | NODD_RHILE |
| TER1_ECOLI | NOD1_RHIGA | MALI_ECOLI | NOD3_RHIME |
| RPC_BP163 | NAHR_PSEPU | EBGR_ECOLI | NOD2_RHISN |
| RBTR_KLEAE | GALR_SALTY | CSCR_ECOLI | NOD2_BRAJA |
| YD28_METTH | GALR_ECOLI | CRP_HAEIN | MALR_STRCO |
| RDGA_ERWCA | FIS_ECOLI | YO14_ARCFU | HRDA_STRCO |
| RPC2_BPP22 | FADR_HAEIN | XTMA_BACSU | HM05_CAEEL |
| HLYX_ACTPL | FX24_RHILV | SCRR_PEDPE | YOAE_ECOLI |
| FNR_SALTY | ENDR_PAEPO | RPC2_LAMBD | Y4CK_RHISN |
| FNR_HAEIN | YCJW_ECOLI | RPC2_BP434 | Y0FO_MYCTU |
| FNR_ECOLI | TNP7_ECOLI | RP54_SALTY | TYRR_HAEIN |
| ETRA_SHEPU | TNP5_PSEAE | RP54_KLEPN | TYRR_ECOLI |
| RPSD_HAEIN | NTRC_AZOBR | RP54_ECOLI | TRA6_PSEAE |
| RP54_PSEPU | MTE8_ECOLI | RP54_BRAJA | RPSD_PSEPU |
| RP54_PSEAE | CRP_SALTY | NOD2_BRAEL | RPSD_CAUCR |
| RP54_AZOVI | CRP_ECOLI | NOD1_RHISN | RPSD_BACSU |
| TER2_ECOLI | ASCG_ECOLI | NOD1_BRASN | RP54_THIFE |
| RPSD_STAAU | ADA_ECOLI | NOD1_BRAJA | NOD2_RHILP |
| RPSD_LEPIN | RP54_ALCEU | MALR_STRPN | NIFA_RHOCA |
| RPSD_ENTFA | GALS_ECOLI | MALI_VIBFU | NIFA_ENTAG |
| RPSA_BACSU | SCRR_VIBAL | GNTR_ECOLI | NIFA_AZOVI |
| DEOR_ECOLI | RP55_RHIME | DBNE_BPD10 | NIFA_AZOCH |
| BIRA_SALTY | RP54_RHIME | Y558_METJA | MERR_STAAU |
| BIRA_ECOLI | RP28_BACTK | Y4WC_RHISN | ILVY_SALTY |
| YP60_METTM | REGA_CLOAB | Y4AM_RHISN | ILVY_ECOLI |
| PARB_ECOLI | NODD_BRASP | Y272_METJA | FECI_ECOLI |
| NTRC_RHIME | CCPA_STRMU | TRPI_PSESY | CYTR_ECOLI |
| NOD2_RHIME | ASNC_ECOLI | TRPI_PSEAE | BTR_BORPE |
| NOD1_RHIME | SCRR_STAXY | RPSD_STRAU | ARAC_ERWCH |
| TER8_PASMU | RPSK_BACSU | RP54_VIBAN | AMPR_ENTCL |
| RPSD_LISMO | RPSD_CLOAB | RP54_ACICA | AMPR_CITFR |
| RCRO_BPP22 | RBSR_BACSU | RCRO_LAMBD | |
| FNRL_RHOSH | KDGR_BACSU | RCRO_BP434 | |
| FIXK_RHIME | DEGA_BACSU | RAFR_ECOLI | |
| FIXK_AZOCA | ASNC_HAEIN | NODD_RHILV | |
| TER8_PASPI | VR2B_BPT4 | NODD_RHILT | |
| TER4_ECOLI | VPB_BPMU | NOD1_BRAEL | |
| RPC1_BP434 | SCRR_STRMU | NIFA_KLEPN | |

Starting now with the set of all 193 discovered sequence fragments, one more iteration of the described method was carried out using this set as the new training set, T. The training set for this iteration was formed by collecting the individual sequence fragments whose support exceeded threshold. As before, the Teiresias parameters were set to L=5 and W=10 whereas the successive threshold choices were K=193/5=38, K=7 and K=2. Sub-selecting those patterns whose estimated log-probability was equal to −30.0 or less produced 1,061 patterns which were added to the previous set of 517 to form a new augmented composite descriptor. The DFA resulting from the latter descriptor was applied to RAND-Swiss-Prot. Of the 537 sequence fragments that received non-zero support, 534 received support 9 or less thus establishing the value 10 as the new $Thres_{rand}$ (=99.2-th percentile). Processing Swiss-Prot with this last DFA, an additional 96 sequence fragments were discovered that exceeded threshold for a grand total of 289 fragments. Table 9 here lists the labels for this additional set of fragments. Table 9 shows the Swiss-Prot labels of the additional 96 sequence fragments that are discovered after augmenting the original composite descriptor with the patterns that are discovered from treating the first set of 193 discovered fragments as a training set.

TABLE 9

| 1 through 25 | 26 through 50 | 51 through 75 | 76 through 96 |
|---|---|---|---|
| HRDB_STRCO | CCPA_BACSU | FNRA_PSEST | VMEM_PVSP |
| EMRD_ECOLI | CCPA_BACME | ANR_PSEAE | V57A_BPT4 |
| HRDD_STRCO | YJGS_ECOLI | YH93_ARCFU | SP3D_BACSU |

TABLE 9-continued

| 1 through 25 | 26 through 50 | 51 through 75 | 76 through 96 |
|---|---|---|---|
| RPSD_LACLA | RP32_VIBCH | RPOS_VIBCH | RPC_BPP2 |
| RPSD_SYNP7 | RBSR_HAEIN | RPOS_PSEAE | MALR_STAXY |
| RPSD_MICAE | YFED_ECOLI | YFER_ECOLI | EBSC_ENTFA |
| RPSD_ANASP | RPSD_RICPR | Y701_SYNY3 | VG36_BPML5 |
| RPSD_AGRTU | RPSD_BORBU | Y4BA_RHISN | VG36_BPMD2 |
| Y01W_MYCTU | RPSD_HELPY | RP32_PSEAE | PRPR_SALTY |
| RPSD_CHLTR | YYAA_BACSU | FRVR_ECOLI | MERB_SERMA |
| RPSD_MYXXA | RP54_XANCV | ARAC_SALTY | BRPA_STRHY |
| RPSD_TREPA | SACR_LACLA | YG27_ARCFU | ARAC_ECOLI |
| RPSD_RHOCA | NIFA_RHISN | XYLR_BACSU | ARAC_CITFR |
| YVDE_BACSU | NIFA_RHIET | RPSC_ANASP | ACOR_ALCEU |
| RPSW_STRCO | NIFA_BRAJA | NADR_KLEPN | YYAG_BACSU |
| Y151_METJA | NFXB_PSEAE | YRDX_RHOSH | YSCC_YEREN |
| RPOS_YEREN | TRA6_BACST | YAHB_ECOLI | XYS4_PSEPU |
| RPOS_SHIFL | RP54_BACSU | TRA4_EACFR | XYS1_PSEPU |
| RPOS_SALTY | ACRR_ECOLI | RPSC_SYNY3 | XYLS_PSEPU |
| RPOS_SALTI | YFET_ECOLI | RP32_CAUCR | THCR_RHOSN |
| RPOS_SALDU | RP54_TREPA | NIFA_AZOLI | TETP_CLOPE |
| RPOS_ECOLI | EXPR_ERWCH | NIFA_AZOBR | |
| PEPR_LACDL | ECHR_ERWCH | MLTD_ECOLI | |
| GALR_HAEIN | SORC_KLEPN | AADR_RHOPA | |
| CCPA_STAXY | RP54_RHOCA | YDT6_SCHPO | |

An analysis of the additional hits using the feature tables in Swiss-Prot showed that 81 of those are true positives, 4 are listed as DNA binding (TRA4_BACFR,V57A_BPT4, NADR_KLEPN) or transcription regulation proteins (EBSC_ENTFA), and 2 are listed as hypothetical proteins (YFED_ECOLI, YDT6_SCHPO). Finally, 8 hits probably correspond to false positives (Y4BA_RHISN, EMRD_ECOLI, VG36_BPMD2, VG36_BPML5, TETP_CLOPE, YSCC_YEREN, MERB_SERMA, MLTD_ECOLI).

A Fourth Example

Searching the C. elegans Genome for EF1G, GPCR and HTH Candidates

The three composite descriptors were used to search the collection of 19,099 ORFs that were reported for the C. elegans genome, by the Washington University in St. Louis, School of Medicine, Genome Sequence Center, as of Jun. 13, 1999. In all three cases, the corresponding values of $Thres_{rand}$ that were established by searching RAND-Swiss-Prot were used.

Elongation Factor 1 Gamma Chain

First, this ORF collection was searched using the 2,260 pattern composite descriptor that was built for the elongation factor gamma chain (PS50040 above). Of the 13 ORFs that received non-zero support only one, F17C11.9, exceeded threshold. This ORF is the one listed in Swiss-Prot (and in PS50040) as EF1G_CAEEL.

G-Protein Coupled Receptors

Next, the C. elegans genome was searched using the composite descriptor for the G protein-coupled receptor that comprised 1,703 patterns. Note that for this particular experiment, it was not set out to discover and enumerate all putative G-protein coupled receptors in C. elegans but rather to show that even when starting with a small knowledge base that contains no GPCR sequences from the genome under consideration it can be effective to mine a complete genome such as C. elegans.

In Table 10 below, the labels of the 101 C. elegans ORFs whose support exceeded threshold are shown. For each of those ORFs, the Score and the P and N values are shown for the top scoring sequence obtained from running a BLASTP search against the set of 804 Swiss-Prot Rel. 35.0 sequences that are known to be true GPCRs (see also discussion above). Table 10 shows the 101 ORFs from C. elegans that were discovered using a composite descriptor for the GPCR family and whose support exceeds threshold. For each of the reported ORFs, also listed are the top scoring sequence from running blastp against the set of 804 Swiss-Prot Rel. 35 sequences that are known to be true GPCRs.

TABLE 10

| # | C. elegans ORF Label | Top Scoring Training Set Seq. | Score | P | N |
|---|---|---|---|---|---|
| 1 | M03F4.3 | 5H1A_MOUSE | 190 | 2.300E−73 | 6 |
| 2 | K09G1.4 | D3DR_RAT | 272 | 4.100E−79 | 6 |
| 3 | K02F2.6 | OAR_DROME | 235 | 1.200E−59 | 5 |
| 4 | F14D12.6 | 5H1A_MOUSE | 214 | 7.300E−77 | 6 |
| 5 | C09B7.1 | 5H1A_MOUSE | 265 | 1.000E−61 | 4 |
| 6 | C02D4.2 | OAR_DROME | 292 | 3.100E−11 | 5 |
| 7 | ZK4SS.3 | GRPR_MOUSE | 181 | 6.600E−38 | 5 |
| 8 | C52B11.3 | 5H1A_MOUSE | 232 | 6.200E−64 | 5 |
| 9 | F15A8.5 | DOP1_DROME | 300 | 6.400E−85 | 3 |
| 10 | F16D3.7 | 5H1A_MOUSE | 202 | 5.400E−44 | 4 |
| 11 | F59C12.2 | 5H2A_CRIGR | 221 | 5.600E−65 | 4 |
| 12 | T14E8.3 | D3DR_RAT | 231 | 4.400E−51 | 4 |
| 13 | T02E9.3 | D3DR_RAT | 190 | 1.600E−43 | 5 |
| 14 | F01E11.5 | OAR_DROME | 293 | 1.400E−77 | 3 |
| 15 | C53C7.1 | NY4R_MOUSE | 177 | 2.800E−36 | 4 |
| 16 | C30F12.6 | SSR4_RAT | 119 | 9.600E−30 | 4 |
| 17 | Y40H4A.a | ACM3_PIG | 485 | 5.100E−83 | 2 |
| 18 | F41E7.3 | NK2R_RAT | 148 | 3.600E−39 | 5 |
| 19 | C38C10.1 | NK1R_RANCA | 232 | 1.800E−59 | 4 |
| 20 | ZC412.1 | NY4R_MOUSE | 176 | 2.500E−30 | 4 |
| 21 | C26F1.6 | OPSB_ANOCA | 71 | 5.200E−10 | 3 |
| 22 | C39B10.1 | AG2R_HUMAN | 68 | 1.800E−04 | 2 |
| 23 | C24A8.1 | D3DR_RAT | 147 | 8.500E−40 | 5 |
| 24 | T07D4.1 | NK1R_RANCA | 114 | 2.900E−27 | 5 |
| 25 | F55E10.7 | OPRX_PIG | 113 | 1.400E−15 | 3 |
| 26 | C16D6.2 | NY4R_MOUSE | 180 | 6.400E−32 | 4 |
| 27 | C10C6.2 | NY4R_MOUSE | 170 | 4.500E−31 | 3 |
| 28 | C15B12.5 | ACM1_RAT | 170 | 7.700E−50 | 7 |
| 29 | F47D12.2 | ACM3_CHICK | 178 | 2.000E−49 | 4 |
| 30 | T23C6.5 | GRPR_MOUSE | 102 | 1.600E−25 | 5 |
| 31 | W05B5.2 | GRPR_MOUSE | 143 | 2.400E−31 | 7 |
| 32 | T27D1.3 | NK1R_RAT | 90 | 3.000E−25 | 5 |
| 33 | C49A9.7 | NK1R_RAT | 318 | 1.400E−65 | 2 |

TABLE 10-continued

| # | C. elegans ORF Label | Top Scoring Training Set Seq. | Score | P | N |
|---|---|---|---|---|---|
| 34 | AH9.1 | OPSB_GECGE | 62 | 6.600E−07 | 3 |
| 35 | B0563.6 | ACM1_RAT | 94 | 3.500E−09 | 3 |
| 36 | R106.2 | SSR4_RAT | 126 | 2.200E−43 | 5 |
| 37 | M01E10.1 | IL8A_RAT | 134 | 2.100E−14 | 1 |
| 38 | T07D10.2 | V1BR_HUMAN | 140 | 2.300E−33 | 6 |
| 39 | F54D7.3 | GRHR_HUMAN | 205 | 3.300E−42 | 4 |
| 40 | C50F7.1 | NK1R_RAT | 183 | 2.000E−35 | 5 |
| 41 | R13H7.2 | 5H1A_MOUSE | 67 | 1.600E−04 | 2 |
| 42 | Y54E2A.1 | SSR4_RAT | 118 | 1.500E−39 | 5 |
| 43 | T07F8.2 | OPRX_PIG | 74 | 4.000E−11 | 4 |
| 44 | C39E6.6 | NY4R_MOUSE | 232 | 9.400E−43 | 4 |
| 45 | K10B4.4 | SSR4_RAT | 97 | 6.400E−30 | 4 |
| 46 | T05A1.1 | NY4R_MOUSE | 218 | 1.700E−30 | 2 |
| 47 | T02E9.1 | GPRO_HUMAN | 106 | 1.600E−23 | 7 |
| 48 | F42C5.2 | SSR4_RAT | 109 | 1.500E−23 | 5 |
| 49 | F35G8.1 | NY4R_MOUSE | 136 | 5.800E−32 | 4 |
| 50 | K03H6.1 | OPRX_PIG | 51 | 5.900E−07 | 5 |
| 51 | F47D12.1 | ACM3_CHICK | 104 | 1.100E−15 | 3 |
| 52 | C56G3.1 | AG2R_HUMAN | 188 | 1.400E−26 | 3 |
| 53 | T23B3.4 | 5H1A_MOUSE | 84 | 1.800E−24 | 5 |
| 54 | AC7.1 | NK1R_RAT | 195 | 4.400E−46 | 3 |
| 55 | C51E3.1 | OLF5_RAT | 83 | 1.800E−08 | 1 |
| 56 | C25G6.5 | NY4R_MOUSE | 208 | 4.600E−42 | 4 |
| 57 | C18B10.4 | PAFR_CAVPO | 51 | 6.100E−02 | 2 |
| 58 | C24A8.4 | 5HTB_DROME | 102 | 1.500E−14 | 2 |
| 59 | T19B10.10 | NK2R_RAT | 84 | 1.000E−07 | 4 |
| 60 | F14F4.1 | V1BR_HUMAN | 109 | 2.100E−25 | 5 |
| 61 | T02D1.6 | GPRO_HUMAN | 103 | 9.800E−18 | 4 |
| 62 | C51E3.2 | OPSD_CATBO | 80 | 4.200E−07 | 2 |
| 63 | Y59E9.118.b | AA3R_HUMAN | 60 | 9.200E−04 | 1 |
| 64 | H02I12.3 | AA1R_CHICK | 86 | 6.300E−13 | 4 |
| 65 | F56B6.5 | SSR4_RAT | 119 | 4.500E−35 | 5 |
| 66 | Y116A8B.5 | SSR4_RAT | 113 | 7.100E−23 | 5 |
| 67 | C44B7.6 | GRHR_HUMAN | 38 | 1.800E−01 | 3 |
| 68 | Y24D9A.29.e | GU03_RAT | 51 | 4.900E−03 | 2 |
| 69 | T22D1.12 | NY4R_MOUSE | 210 | 4.500E−41 | 4 |
| 70 | R12C12.3 | NY4R_MOUSE | 57 | 3.000E−07 | 4 |
| 71 | F21C10.9 | SSR4_RAT | 71 | 2.500E−10 | 4 |
| 72 | F59A1.12 | CRFR_CHICK | 42 | 3.600E−01 | 3 |
| 73 | F40A3.7 | AA1R_CAVPO | 47 | 1.300E−03 | 3 |
| 74 | T19F4.1 | ML1C_CHICK | 62 | 6.600E−09 | 4 |
| 75 | F59B2.13 | SSR4_RAT | 71 | 1.900E−05 | 3 |
| 76 | F54E4.1 | CASR_HUMAN | 51 | 9.000E−01 | 1 |
| 77 | F54D1.5 | CASR_HUMAN | 49 | 8.200E−01 | 1 |
| 78 | C54A12.2 | OPSB_ANOCA | 58 | 7.400E−08 | 3 |
| 79 | C53A5.12 | ACM3_RAT | 275 | 1.400E−33 | 1 |
| 80 | Y58G8A.208.a | NY4R_MOUSE | 186 | 4.600E−38 | 4 |
| 81 | Y105C5.v | EBI2_HUMAN | 129 | 9.700E−17 | 2 |
| 82 | T25B6.2 | NK1R_RAT | 53 | 1.200E−01 | 2 |
| 83 | 522G5.4 | GRPR_MOUSE | 70 | 4.300E−09 | 3 |
| 84 | F31B9.1 | NK1R_RANCA | 106 | 1.000E−27 | 5 |
| 85 | C03G6.13 | ACM2_HUMAN | 46 | 1.400E−01 | 3 |
| 86 | H09F14.1 | SSR4_RAT | 73 | 2.400E−12 | 4 |
| 87 | C45H4.3 | AG2R_HUMAN | 46 | 1.400E−01 | 2 |
| 88 | Y71G12A.199. | VIPR_MELGA | 51 | 4.100E−02 | 2 |
| 89 | T23H2.3 | DOP1_DROME | 55 | 2.200E−01 | 1 |
| 90 | F59A7.8 | NK1R_RANCA | 52 | 2.300E−01 | 1 |
| 91 | F55D10.4 | MC4R_RAT | 67 | 6.800E−07 | 4 |
| 92 | F21G4.2 | OAR_DROME | 53 | 3.400E−01 | 1 |
| 93 | C15H11.2 | V1BR_HUMAN | 89 | 5.900E−20 | 5 |
| 94 | C10F3.3 | OL1J_HUMAN | 46 | 1.200E−02 | 4 |
| 95 | C06B3.11 | B3AR_MOUSE | 53 | 1.700E−04 | 3 |
| 96 | Y77E11A.3443 | MSHR_HUMAN | 59 | 1.000E−02 | 1 |
| 97 | K09C6.5 | MC4R_RAT | 41 | 5.200E−02 | 3 |
| 98 | Y41D4B.3805. | GRHR_HUMAN | 70 | 1.600E−04 | 1 |
| 99 | Y40H7.d | OAR_DROME | 37 | 9.700E−01 | 1 |
| 100 | Y116F11.zz8 | SSR4_RAT | 53 | 4.800E−02 | 2 |
| 101 | T26E4.15 | AG2R_HUMAN | 79 | 2.400E−09 | 3 |

In addition to the above 101 C. elegans ORFs that exceeded threshold and as testimony to the stringent thresholds use, there is also listed in Table 11 below an additional 19 ORFs whose scores were just below threshold and which generated blast-search P values that were significant. As before, the blast searches were carried out against the set of 804 Swiss-Prot Rel. 35.0 known true GPCRs. Table 11 shows an additional 19 ORFs from C. elegans that receive scores just below threshold but show significant blast-search P values when compared against the set of 804 true GPCRs from Rel. 35.0 of Swiss-Prot.

TABLE 11

| # | C. elegans ORF Label | Top Scoring Training Set Seq. | Score | P | N |
|---|---|---|---|---|---|
| 102 | T26E4.14 | AG2R_HUMAN | 73 | 8.10E−08 | 2 |
| 103 | M01B2.7 | NK1R_RANCA | 60 | 4.10E−09 | 4 |
| 104 | K03H6.5 | SSR4_RAT | 52 | 6.50E−05 | 4 |
| 105 | F58D7.1 | SSR4_RAT | 55 | 9.50E−06 | 4 |
| 106 | F57H12.4 | D3DR_RAT | 80 | 9.40E−10 | 3 |
| 107 | F53A9.5 | AA1R_CAVPO | 78 | 5.50E−06 | 1 |
| 109 | F02E8.2 | SSR4_RAT | 90 | 6.50E−21 | 5 |
| 110 | C51E3.4 | OPSD_CATBO | 83 | 3.10E−06 | 1 |
| 111 | C02H7.2 | 5H2A_CRIGR | 61 | 8.00E−09 | 4 |
| 113 | Y34D9A.152.d | NY4R_MOUSE | 56 | 2.10E−08 | 4 |
| 114 | K06B4.9 | ML1X_HUMAN | 73 | 2.60E−06 | 2 |
| 118 | F37E3.2 | GPCR_LYMST | 127 | 2.70E−11 | 3 |
| 119 | F35F10.2 | PAFR_CAVPO | 51 | 8.50E−04 | 3 |
| 124 | C06G4.5 | OPRX_PIG | 164 | 3.50E−23 | 4 |
| 128 | Y57A10C.8 | OLF9_RAT | 65 | 2.80E−04 | 2 |
| 132 | Y4C6A.h | MGR8_HUMAN | 347 | 2.30E−215 | 1 |
| 134 | R07B5.5 | A2AA_PIG | 53 | 1.40E−04 | 3 |
| 135 | M01B2.9 | AG2R_HUMAN | 73 | 1.50E−07 | 2 |
| 140 | C51E3.3 | AA1R_CHICK | 73 | 5.70E−05 | 1 |

Several comments are in order here. First, it should be stressed that the above analysis is not implying that there is only 120 G-protein coupled receptors in C. elegans. Instead, what is attempted to be demonstrated is that even if one begins with a small knowledge base of only 80 known GPCRs that have been selected randomly, one can still build a pretty useful composite descriptor for the family and use it to explore a largely-unexplored genome such as C. elegans. In order to have a complete enumeration of the GPCRs that are present in C. elegans, the composite descriptor should be built by using all of the GPCRs that are present in GPCRDB and not only 80 of them. Second, it was opted to run the BLAST searches against the set of 804 sequences in order to show the ability of the proposed method to extrapolate. As such, blast-search results with P values that are relatively high (e.g. E-02) should not be surprising since the target database of 804 true GPCRs is but a small fraction of the current contents of GPCRDB. Indeed the November 1999 release of GPCRDB contained 1,704 GPCR sequences and 431 GPCR sequence fragments for a grand total of 2,135 entries.

Helix-Turn-Helix

Finally, the 19,099 ORFs of C. elegans was searched for instances of the helix-turn-helix binding motif using the corresponding 2,288 (=1,896+392) pattern composite descriptor. Of the 169 sequences that received non-zero support, only 5 exceeded threshold: Y94H6A__142.g (in the region delineated by a.a. 65 through 95), C16C2.1 (in the region delineated by a.a. 59 through 89), F18C5.2 (in the region delineated by a.a. 850 through 880), Y39F10A.a (in the region delineated by a.a. 125 through 155), Y48C3A.s (in the region delineated by a.a. 113 through 143), and Y48C3A.s (in the region delineated by a.a. 113 through 143), The fragments were:
>Y94H6A__142.g fragment (SEQ ID NO 55)
IFDNTNDLVASLLGISSITVYRKRKRIGEE
>C16C2.1 fragment (SEQ ID NO 56)
YLSGSTRAKLAESLGLSDNQVKVWFQNRRT
>F18C5.2 fragment (SEQ ID NO 57)
ISRSTAKEVATARGISEGTVYSYLAMAVEK >Y39F10A.a fragment (SEQ ID NO 58)
LSAYTISDLAKHFNVSKIEILKIDIEGAEL
>Y48C3A.s fragment (SEQ ID NO 59)
NEVLNLNEVAKELNISKRRVYDVINVLEGL and their respective top-scoring sequences from the training set of 70 helix-turn helix segments, blast scores, P and N values are:

| # | *C. elegans* ORF | Top Scoring | Scor | P | N |
|---|---|---|---|---|---|
| 1 | Y94H6A_142.g | RPSF_BACSU | 50 | 2.80E−06 | 1 |
| 2 | C16C2.1 | TER3_ECOLI | 45 | 1.30E−05 | 1 |
| 3 | F18C5.2 | VBP_BPMU | 47 | 9.30E−06 | 1 |

-continued

| # | *C. elegans* ORF | Top Scoring | Scor | P | N |
|---|---|---|---|---|---|
| 4 | Y39F10A.a | TNP0_ECOLI | 39 | 1.10E−04 | 1 |
| 5 | Y48C3A.s | TNP1_ECOLI | 49 | 6.40E−06 | 1 |

It is to be understood that the embodiments and variations shown and described herein are merely illustrative of the principles of this invention and that various modifications may be implemented by those skilled in the art without departing from the scope and spirit of the invention.

---

What is claimed is:

1. A method comprising the steps of:
   providing a set of sequences, wherein:
      the sequences are not aligned; and
      each sequence comprises a series of symbols;
   discovering a plurality of patterns common to a plurality of the sequences, wherein each pattern comprises a plurality of positions, at least one of the positions comprise an expected symbol and at least one of the positions comprise one symbol of a specified plurality of symbols, wherein the specified plurality of symbols consists of at least two symbols and no more than $|\Sigma|-1$ symbols, wherein $|\Sigma|$ is a number of available symbols in a set of amino acids, wherein $\Sigma$ consists of A, C, D, E, F, G, H, I, K, L, M, N, P, Q, R, S, T, V, W and Y; and
   determining if a candidate sequence comprises a predetermined number of the patterns; and
   storing the plurality of patterns in a data storage device.

2. The method of claim 1, wherein the patterns common to a plurality of the set of sequences comprise test patterns, wherein the sequences in set of sequences comprise test sequences, and wherein the step of determining if a candidate sequence comprises a predetermined number of the patterns comprises the step of determining if there are candidate patterns in the candidate sequence that match all of the predetermined number of test patterns.

3. The method of claim 1, further comprising the step of determining if each of the plurality of patterns is statistically significant.

4. The method of claim 3, wherein the step of determining if each of the plurality of patterns is statistically significant comprises the steps of selecting one of the patterns, determining if a probability that the selected pattern occurs in a sequence meets a predetermined threshold, and continuing to select additional patterns until each pattern has been selected.

5. The method of claim 4, wherein the step of determining if a probability that the selected pattern occurs in a sequence meets a predetermined threshold further comprises the steps of using a second-order Markov chain method to determine the probability that the selected pattern occurs in a sequence and determining a natural logarithm of the probability that the selected pattern occurs in a sequence.

6. The method of claim 3, wherein the step of determining if each of the plurality of patterns is statistically significant further comprises the steps of removing instances of each of the patterns from the set of sequences to create a new set of sequences and performing the step of discovering on the new set of sequences.

7. The method of claim 3, wherein the step of determining if each of the plurality of patterns is statistically significant further comprises the steps of if any of the patterns is statistically significant, selecting a statistically significant pattern, modifying a composite descriptor to include the selected pattern if the selected pattern is not already part of the composite descriptor, and continuing to select statistically significant patterns until all statistically significant patterns have been selected.

8. The method of claim 1, wherein the step of discovering is performed without using any knowledge about biological information related to family, cardinality or image characteristics of sequences in the set of unaligned sequences.

9. The method of claim 1, further comprising the steps of:
   if the candidate sequence comprises the predetermined number of patterns, adding the candidate sequence to the set of sequences to create a new set of sequences; and
   performing the step of discovering on the new set of sequences.

10. The method of claim 1, wherein some of the plurality of positions comprise positions which may be occupied by any sequence character.

11. The method of claim 1, wherein the step of discovering a plurality of patterns common to a plurality of the sequences comprises the steps of:
   selecting a predetermined threshold that indicates how many of the sequences should contain a pattern for the pattern to be considered common;

discovering patterns, if any, that are common to the predetermined threshold of sequences;

if there are no patterns common to the predetermined threshold of sequences, decreasing the predetermined threshold; and performing, until the predetermined threshold is less than a predetermined amount, the step of discovering patterns, if any, that are common to the predetermined threshold of sequences and the step of if there are no patterns common to the predetermined threshold of sequences, decreasing the predetermined threshold.

12. A system comprising:

a memory that stores computer-readable code; and a processor operatively coupled to said memory, said processor configured to implement said computer-readable code, said computer-readable code configured to:
provide a set of sequences, wherein:
the sequences are not aligned; and
each sequence comprises a series of symbols;
discover a plurality of patterns common to a plurality of the sequences, wherein each pattern comprises a plurality of positions, at least one of the positions comprise an expected symbol and at least one of the positions comprise one symbol of a specified plurality of symbols, wherein the specified plurality of symbols consists of at least two symbols and no more than $|\Sigma|-1$ symbols, wherein $|\Sigma|$ is a number of available symbols in a set of amino acids, and wherein $\Sigma$ consists of A, C, D, E, F, G, H, I, K, L, M, N, P, Q, R, S, T, V, W and Y;
determine if a candidate sequence comprises a predetermined number of the patterns; and
store the plurality of patterns in a data storage device.

13. An article of manufacture comprising:

a computer readable medium having computer readable code means embodied thereon, said computer readable program code means comprising:
a step to provide a set of sequences, wherein:
the sequences are not aligned; and
each sequence comprises a series of symbols;
a step to discover a plurality of patterns common to a plurality of the sequences, wherein each pattern comprises a plurality of positions, at least one of the positions comprise an expected symbol and at least one of the positions comprise one symbol of a specified plurality of symbols, wherein the specified plurality of symbols consists of at least two symbols and no more than $|\Sigma|-1$ symbols, wherein $|\Sigma|$ is a number of available symbols in a set of amino acids, and wherein $\Sigma$ consists of A, C, D, E, F, G, H, I, K, L, M, N, P, Q, R, S, T, V, W and Y;
a step to determine if a candidate sequence comprises a predetermined number of the patterns; and
store the plurality of patterns in a data storage device.

* * * * *

SEQUENCE LISTING

```
<160> NUMBER OF SEQ ID NOS: 59

<210> SEQ ID NO 1
<211> LENGTH: 60
<212> TYPE: PRT
<213> ORGANISM: Xenopus laevis

<400> SEQUENCE: 1

Met Ala Gly Gly Thr Leu Tyr Thr Tyr Pro Asp Asn Trp Arg Ala Tyr
1               5                   10                  15

Lys Pro Leu Ile Ala Ala Gln Tyr Ser Gly Phe Pro Ile Lys Val Ala
            20                  25                  30

Ser Ser Ala Pro Glu Phe Gln Phe Gly Val Thr Asn Lys Thr Pro Glu
        35                  40                  45

Phe Leu Lys Lys Phe Pro Leu Gly Lys Val Pro Ala
    50                  55                  60

<210> SEQ ID NO 2
<211> LENGTH: 60
<212> TYPE: PRT
<213> ORGANISM: Fugu rubripes
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (11)..(22)
<223> OTHER INFORMATION: Xaa can be any naturally occurring amino acid
<220> FEATURE:
<221> NAME/KEY: misc_feature
<222> LOCATION: (39)..(60)
<223> OTHER INFORMATION: Xaa can be any naturally occurring amino acid

<400> SEQUENCE: 2

Met Ala Xaa Xaa Thr Leu Tyr Val Ser Pro Xaa Xaa Xaa Xaa Xaa Xaa
1               5                   10                  15

Xaa Xaa Xaa Xaa Xaa Xaa His Leu Asp Asp Phe Arg Ser Leu Leu Ala
            20                  25                  30

Leu Val Ala Ala Glu Tyr Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 3
```

```
<211> LENGTH: 60
<212> TYPE: PRT
<213> ORGANISM: Xenopus laevis

<400> SEQUENCE: 3

Phe Glu Gly Lys Asp Gly Phe Cys Leu Phe Glu Ser Ser Ala Ile Ala
1               5                   10                  15

His Tyr Val Gly Asn Asp Glu Leu Arg Gly Thr Thr Arg Leu His Gln
            20                  25                  30

Ala Gln Val Ile Gln Trp Val Ser Phe Ser Asp Ser His Ile Val Pro
        35                  40                  45

Pro Ala Ser Ala Trp Val Phe Pro Thr Leu Gly Ile
    50                  55                  60

<210> SEQ ID NO 4
<211> LENGTH: 60
<212> TYPE: PRT
<213> ORGANISM: Fugu rubripes
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(19)
<223> OTHER INFORMATION: Xaa can be any naturally occurring amino acid
<220> FEATURE:
<221> NAME/KEY: misc_feature
<222> LOCATION: (25)..(31)
<223> OTHER INFORMATION: Xaa can be any naturally occurring amino acid

<400> SEQUENCE: 4

Xaa Xaa Xaa Xaa Xaa Xaa Xaa Cys Xaa Xaa Xaa Xaa Xaa Xaa Xaa Xaa
1               5                   10                  15

Xaa Xaa Xaa Gly Asn Ala Lys Gln Xaa Xaa Xaa Xaa Xaa Xaa Xaa Gln
            20                  25                  30

Ser Gln Val Trp Gln Trp Leu Ser Phe Ala Asp Asn Glu Leu Thr Pro
        35                  40                  45

Val Ser Cys Ala Val Val Phe Pro Leu Met Gly Met
    50                  55                  60

<210> SEQ ID NO 5
<211> LENGTH: 60
<212> TYPE: PRT
<213> ORGANISM: Xenopus laevis

<400> SEQUENCE: 5

Met Gln Tyr Asn Lys Gln Ala Thr Glu Gln Ala Lys Glu Gly Ile Lys
1               5                   10                  15

Thr Val Leu Gly Val Leu Asp Ser His Leu Gln Thr Arg Thr Phe Leu
            20                  25                  30

Val Gly Glu Arg Ile Thr Leu Ala Asp Ile Thr Val Thr Cys Ser Leu
        35                  40                  45

Leu Trp Leu Tyr Lys Gln Val Leu Glu Pro Ser Phe
    50                  55                  60

<210> SEQ ID NO 6
<211> LENGTH: 60
<212> TYPE: PRT
<213> ORGANISM: Fugu rubripes

<400> SEQUENCE: 6

Thr Gly Leu Asp Lys Lys Ile Gln Gln Asn Ser Arg Val Glu Leu Met
```

```
                1               5                  10                   15
        Arg Val Leu Lys Val Leu Asp Gln Ala Leu Glu Pro Arg Thr Phe Leu
                        20                  25                  30

Val Gly Glu Ser Ile Thr Leu Ala Asp Met Ala Val Ala Met Ala Val
                        35                  40                  45

Leu Leu Pro Phe Lys Tyr Val Leu Glu Pro Ser Asp
                        50                  55                  60

<210> SEQ ID NO 7
        <211> LENGTH: 60
        <212> TYPE: PRT
        <213> ORGANISM: Xenopus laevis

<400> SEQUENCE: 7

Arg Gln Pro Phe Gly Asn Val Thr Arg Trp Phe Val Thr Cys Val Asn
        1               5                   10                  15

Gln Pro Glu Phe Arg Ala Val Leu Gly Glu Val Lys Leu Cys Asp Lys
                        20                  25                  30

Met Ala Gln Phe Asp Ala Lys Lys Phe Ala Glu Met Gln Pro Lys Lys
                        35                  40                  45

Glu Thr Pro Lys Lys Glu Lys Pro Ala Lys Glu Pro
                        50                  55                  60

<210> SEQ ID NO 8
        <211> LENGTH: 59
        <212> TYPE: PRT
        <213> ORGANISM: Fugu rubripes

<400> SEQUENCE: 8

Arg Asn Val Leu Met Asn Val Thr Arg Trp Phe Thr Thr Cys Ile Asn
        1               5                   10                  15

Gln Pro Glu Phe Leu Lys Val Leu Gly Lys Ile Ser Leu Cys Glu Lys
                        20                  25                  30

Met Val Pro Val Thr Ala Lys Thr Ser Thr Glu Glu Ala Ala Ala Val
                        35                  40                  45

His Pro Asp Ala Ala Ala Leu Asn Gly Pro Pro
                        50                  55

<210> SEQ ID NO 9
        <211> LENGTH: 60
        <212> TYPE: PRT
        <213> ORGANISM: Xenopus laevis
        <220> FEATURE:
        <221> NAME/KEY: misc_feature
        <222> LOCATION: (44)..(44)
        <223> OTHER INFORMATION: Xaa can be any naturally occurring amino acid

<400> SEQUENCE: 9

Lys Lys Glu Lys Glu Glu Lys Lys Ala Ala Pro Thr Pro Ala Pro
        1               5                   10                  15

Ala Pro Glu Asp Asp Leu Asp Glu Ser Glu Lys Ala Leu Ala Ala Glu
                        20                  25                  30

Pro Lys Ser Lys Asp Pro Tyr Ala His Leu Pro Xaa Lys Ser Ser Phe
                        35                  40                  45

Ile Met Asp Glu Phe Lys Arg Lys Tyr Ser Asn Glu
                        50                  55                  60

<210> SEQ ID NO 10
        <211> LENGTH: 60
        <212> TYPE: PRT
```

<213> ORGANISM: Fugu rubripes

<400> SEQUENCE: 10

Lys Thr Glu Ala Gln Leu Lys Lys Glu Ala Lys Lys Arg Glu Lys Leu
1               5                   10                  15

Glu Lys Phe Gln Gln Lys Lys Glu Met Glu Ala Lys Lys Lys Met Gln
                20                  25                  30

Pro Val Ala Glu Lys Lys Ala Lys Pro Glu Lys Arg Glu Leu Gly Val
                35                  40                  45

Ile Thr Tyr Asp Ile Pro Thr Pro Ser Gly Glu Lys
        50                  55                  60

<210> SEQ ID NO 11
<211> LENGTH: 60
<212> TYPE: PRT
<213> ORGANISM: Xenopus laevis
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid

<400> SEQUENCE: 11

Asp Thr Leu Thr Val Ala Leu Pro Tyr Phe Trp Xaa Glu His Phe Asp
1               5                   10                  15

Lys Glu Gly Trp Ser Ile Trp Tyr Ala Glu Tyr Xaa Lys Phe Pro Glu
                20                  25                  30

Glu Leu Thr Gln Ala Phe Met Ser Cys Asn Leu Ile Thr Gly Met Phe
                35                  40                  45

Gln Arg Xaa Leu Asp Lys Leu Arg Lys Thr Gly Phe
        50                  55                  60

<210> SEQ ID NO 12
<211> LENGTH: 60
<212> TYPE: PRT
<213> ORGANISM: Fugu rubripes

<400> SEQUENCE: 12

Lys Asp Val Val Ser Pro Leu Pro Asp Ser Tyr Ser Pro Gln Tyr Val
1               5                   10                  15

Glu Ala Ala Trp Tyr Pro Trp Trp Glu Lys Gln Gly Phe Phe Lys Pro
                20                  25                  30

Glu Phe Gly Arg Lys Ser Ile Gly Glu Gln Asn Pro Arg Gly Ile Phe
                35                  40                  45

Met Met Cys Ile Pro Pro Pro Asn Val Thr Gly Ser
        50                  55                  60

<210> SEQ ID NO 13
<211> LENGTH: 60
<212> TYPE: PRT
<213> ORGANISM: Xenopus laevis
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature

```
<222> LOCATION: (34)..(38)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid

<400> SEQUENCE: 13

Ala Ser Val Ile Leu Phe Gly Thr Asn Asn Ser Ser Ile Ser Gly
1               5                   10                  15

Val Trp Val Xaa Phe Arg Gly Gln Asp Leu Ala Phe Thr Leu Ser Glu
            20                  25                  30

Asp Xaa Xaa Xaa Xaa Trp Gln Ile Asp Tyr Glu Ser Tyr Asn Trp
        35                  40                  45

Arg Lys Leu Asp Ser Gly Ser Glu Glu Cys Xaa Xaa
    50                  55                  60

<210> SEQ ID NO 14
<211> LENGTH: 60
<212> TYPE: PRT
<213> ORGANISM: Fugu rubripes

<400> SEQUENCE: 14

Leu His Leu Gly His Ala Leu Thr Asn Ala Ile Gln Asp Thr Leu Thr
1               5                   10                  15

Arg Trp His Arg Met Arg Gly Glu Thr Thr Leu Trp Asn Pro Gly Cys
            20                  25                  30

Asp His Ala Gly Ile Ala Thr Gln Val Val Glu Lys Lys Leu Met
        35                  40                  45

Arg Glu Lys Gly Thr Ser Arg His Asp Leu Gly Arg
    50                  55                  60

<210> SEQ ID NO 15
<211> LENGTH: 60
<212> TYPE: PRT
<213> ORGANISM: Xenopus laevis
<220> FEATURE:
<221> NAME/KEY: misc_feature
<222> LOCATION: (14)..(21)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (38)..(60)
<223> OTHER INFORMATION: Xaa can be any naturally occurring amino acid

<400> SEQUENCE: 15

Lys Thr Leu Val Lys Glu Tyr Phe Ala Trp Glu Gly Glu Xaa Xaa Xaa
1               5                   10                  15

Xaa Xaa Xaa Xaa Xaa Phe Lys Asn Val Gly Lys Pro Phe Asn Gln Gly
            20                  25                  30

Xaa Lys Ile Phe Lys Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 16
<211> LENGTH: 60
<212> TYPE: PRT
<213> ORGANISM: Fugu rubripes
```

-continued

```
<400> SEQUENCE: 16

Glu Lys Phe Ile Glu Glu Val Trp Lys Trp Lys Asn Glu Lys Gly Asp
1               5                   10                  15

Arg Ile Tyr His Gln Leu Lys Lys Leu Gly Ser Ser Leu Asp Trp Asp
            20                  25                  30

Arg Ala Cys Phe Thr Met Asp Pro Lys Leu Ser Tyr Ala Val Gln Glu
        35                  40                  45

Ala Phe Ile Arg Met His Asp Glu Gly Val Ile Tyr
    50                  55                  60

<210> SEQ ID NO 17
<211> LENGTH: 60
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 17

Xaa Val Leu Glu Leu Tyr Leu Asp Leu Leu Ser Gln Pro Cys Arg Ala
1               5                   10                  15

Ile Tyr Ile Phe Ala Lys Lys Asn Asn Ile Pro Phe Gln Met His Thr
            20                  25                  30

Val Glu Leu Arg Lys Gly Glu His Leu Ser Asp Ala Phe Ala Arg Val
        35                  40                  45

Asn Pro Met Lys Lys Val Pro Ala Met Met Xaa Asp
    50                  55                  60

<210> SEQ ID NO 18
<211> LENGTH: 60
<212> TYPE: PRT
<213> ORGANISM: Rattus norvegicus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 18

Xaa Val Leu Glu Leu Tyr Leu Asp Leu Leu Ser Gln Pro Cys Arg Ala
1               5                   10                  15

Ile Tyr Ile Phe Ala Lys Lys Asn Asn Ile Pro Phe Gln Met His Thr
            20                  25                  30

Val Glu Leu Arg Lys Gly Glu His Leu Ser Asp Ala Phe Ala Gln Val
        35                  40                  45

Asn Pro Met Lys Lys Val Pro Ala Met Lys Xaa Asp
    50                  55                  60

<210> SEQ ID NO 19
<211> LENGTH: 60
<212> TYPE: PRT
<213> ORGANISM: Artemia salina

<400> SEQUENCE: 19

Val Ala Gly Lys Leu Tyr Thr Tyr Pro Glu Asn Phe Arg Ala Phe Lys
```

```
                1               5                    10                   15
Ala Leu Ile Ala Ala Gln Tyr Ser Gly Ala Lys Leu Glu Ile Ala Lys
                    20                  25                  30

Ser Phe Val Phe Gly Glu Thr Asn Lys Ser Asp Ala Phe Leu Lys Ser
            35                  40                  45

Phe Pro Leu Gly Lys Val Pro Ala Phe Glu Ser Ala
        50                  55                  60

<210> SEQ ID NO 20
<211> LENGTH: 60
<212> TYPE: PRT
<213> ORGANISM: Mus musculus
<220> FEATURE:
<221> NAME/KEY: misc_feature
<222> LOCATION: (19)..(42)
<223> OTHER INFORMATION: Xaa can be any naturally occurring amino acid

<400> SEQUENCE: 20

Gly Gly Phe Thr Leu Cys Glu Ser Val Ala Ile Leu Leu Tyr Leu Ala
1               5                   10                  15

His Lys Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Tyr Lys Val Pro Asp His
        35                  40                  45

Trp Tyr Pro Gln Asp Leu Gln Ala Arg Ala Arg Val
        50                  55                  60

<210> SEQ ID NO 21
<211> LENGTH: 60
<212> TYPE: PRT
<213> ORGANISM: Rattus norvegicus
<220> FEATURE:
<221> NAME/KEY: misc_feature
<222> LOCATION: (19)..(42)
<223> OTHER INFORMATION: Xaa can be any naturally occurring amino acid

<400> SEQUENCE: 21

Gly Gly Phe Thr Leu Cys Glu Ser Val Ala Ile Leu Leu Tyr Leu Ala
1               5                   10                  15

His Lys Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Tyr Lys Val Pro Asp His
        35                  40                  45

Trp Tyr Pro Gln Asp Leu Gln Ala Arg Ala Arg Val
        50                  55                  60

<210> SEQ ID NO 22
<211> LENGTH: 60
<212> TYPE: PRT
<213> ORGANISM: Artemia salina

<400> SEQUENCE: 22

Asp Gly His Cys Ile Ala Glu Ser Asn Ala Ile Ala Tyr Tyr Val Ala
1               5                   10                  15

Asn Glu Thr Leu Arg Gly Ser Ser Asp Leu Glu Lys Ala Gln Ile Ile
            20                  25                  30

Gln Trp Met Thr Phe Ala Asp Thr Glu Ile Leu Pro Ala Ser Cys Thr
        35                  40                  45

Trp Val Phe Pro Val Leu Gly Ile Met Gln Phe Asn
        50                  55                  60
```

<210> SEQ ID NO 23
<211> LENGTH: 60
<212> TYPE: PRT
<213> ORGANISM: Mus musculus

<400> SEQUENCE: 23

```
Asp Glu Tyr Leu Ala Trp Gln His Thr Gly Leu Arg Arg Ser Cys Leu
1               5                   10                  15

Arg Ala Leu Trp His Lys Val Met Phe Pro Val Phe Leu Gly Glu Gln
            20                  25                  30

Ile Pro Pro Glu Thr Leu Ala Ala Thr Leu Ala Glu Leu Asp Val Asn
        35                  40                  45

Leu Gln Val Leu Glu Asp Lys Phe Leu Gln Asp Lys
    50                  55                  60
```

<210> SEQ ID NO 24
<211> LENGTH: 60
<212> TYPE: PRT
<213> ORGANISM: Rattus norvegicus

<400> SEQUENCE: 24

```
Asp Glu Tyr Leu Ala Trp Gln His Thr Thr Leu Arg Arg Ser Cys Leu
1               5                   10                  15

Arg Thr Leu Trp His Lys Val Met Phe Pro Val Phe Leu Gly Glu Gln
            20                  25                  30

Ile Arg Pro Glu Met Leu Ala Ala Thr Leu Ala Asp Leu Asp Val Asn
        35                  40                  45

Val Gln Val Leu Glu Asp Gln Phe Leu Gln Asp Lys
    50                  55                  60
```

<210> SEQ ID NO 25
<211> LENGTH: 60
<212> TYPE: PRT
<213> ORGANISM: Artemia salina

<400> SEQUENCE: 25

```
Lys Gln Ala Thr Ala Arg Ala Lys Glu Asp Ile Asp Lys Ala Leu Gln
1               5                   10                  15

Ala Leu Asp Asp His Leu Leu Thr Arg Thr Tyr Leu Val Gly Glu Arg
            20                  25                  30

Ile Thr Leu Ala Asp Ile Val Val Thr Cys Thr Leu Leu His Leu Tyr
        35                  40                  45

Gln His Val Leu Asp Glu Ala Phe Arg Lys Ser Tyr
    50                  55                  60
```

<210> SEQ ID NO 26
<211> LENGTH: 60
<212> TYPE: PRT
<213> ORGANISM: Mus musculus

<400> SEQUENCE: 26

```
Asp Phe Leu Val Gly Pro His Ile Ser Leu Ala Asp Leu Val Ala Ile
1               5                   10                  15

Thr Glu Leu Met His Pro Val Gly Gly Cys Pro Val Phe Glu Gly
            20                  25                  30

His Pro Arg Leu Ala Ala Trp Tyr Gln Arg Val Glu Ala Ala Val Gly
        35                  40                  45

Lys Asp Leu Phe Arg Glu Ala His Glu Val Ile Leu
    50                  55                  60
```

<210> SEQ ID NO 27
<211> LENGTH: 60
<212> TYPE: PRT
<213> ORGANISM: Rattus norvegicus

<400> SEQUENCE: 27

Asp Phe Leu Val Gly Pro His Ile Ser Leu Ala Asp Val Val Ala Ile
1               5                   10                  15

Thr Glu Leu Met His Pro Val Gly Gly Cys Pro Val Phe Glu Gly
            20                  25                  30

Arg Pro Arg Leu Ala Ala Trp Tyr Arg Arg Val Glu Ala Ala Val Gly
        35                  40                  45

Lys Asp Leu Phe Leu Glu Ala His Glu Val Ile Leu
    50                  55                  60

<210> SEQ ID NO 28
<211> LENGTH: 60
<212> TYPE: PRT
<213> ORGANISM: Artemia salina
<220> FEATURE:
<221> NAME/KEY: misc_feature
<222> LOCATION: (35)..(37)
<223> OTHER INFORMATION: Xaa can be any naturally occurring amino acid

<400> SEQUENCE: 28

Val Asn Thr Asn Arg Trp Phe Ile Thr Leu Ile Asn Gln Lys Gln Val
1               5                   10                  15

Lys Ala Val Ile Gly Asp Phe Lys Leu Cys Glu Lys Ala Gly Glu Phe
            20                  25                  30

Asp Pro Xaa Xaa Xaa Lys Lys Tyr Ala Glu Phe Gln Ala Ala Ile Gly
        35                  40                  45

Ser Gly Glu Lys Lys Lys Thr Glu Lys Ala Pro Lys
    50                  55                  60

<210> SEQ ID NO 29
<211> LENGTH: 60
<212> TYPE: PRT
<213> ORGANISM: Mus musculus
<220> FEATURE:
<221> NAME/KEY: misc_feature
<222> LOCATION: (26)..(60)
<223> OTHER INFORMATION: Xaa can be any naturally occurring amino acid

<400> SEQUENCE: 29

Lys Val Lys Asp Cys Pro Pro Ala Asp Leu Ile Ile Lys Gln Lys Leu
1               5                   10                  15

Met Pro Arg Val Leu Thr Met Ile Gln Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 30
<211> LENGTH: 60
<212> TYPE: PRT
<213> ORGANISM: Rattus norvegicus
<220> FEATURE:
<221> NAME/KEY: misc_feature
<222> LOCATION: (26)..(60)
<223> OTHER INFORMATION: Xaa can be any naturally occurring amino acid -continued

<400> SEQUENCE: 30

Lys Val Arg Asp Cys Pro Pro Ala Asp Pro Val Ile Lys Gln Lys Leu
1               5                   10                  15

Met Pro Arg Val Leu Thr Met Ile Gln Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55                  60

<210> SEQ ID NO 31
<211> LENGTH: 60
<212> TYPE: PRT
<213> ORGANISM: Artemia salina

<400> SEQUENCE: 31

Ala Val Lys Ala Lys Pro Glu Lys Lys Glu Val Pro Lys Lys Glu Gln
1               5                   10                  15

Glu Glu Pro Ala Asp Ala Ala Glu Glu Ala Leu Ala Ala Glu Pro Lys
            20                  25                  30

Ser Lys Asp Pro Phe Asp Glu Met Pro Lys Gly Thr Phe Asn Met Asp
        35                  40                  45

Asp Phe Lys Arg Phe Tyr Ser Asn Asn Glu Glu Thr
    50                  55                  60

<210> SEQ ID NO 32
<211> LENGTH: 60
<212> TYPE: PRT
<213> ORGANISM: Mus musculus
<220> FEATURE:
<221> NAME/KEY: misc_feature
<222> LOCATION: (1)..(60)
<223> OTHER INFORMATION: Xaa can be any naturally occurring amino acid

<400> SEQUENCE: 32

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55                  60

<210> SEQ ID NO 33
<211> LENGTH: 60
<212> TYPE: PRT
<213> ORGANISM: Rattus norvegicus
<220> FEATURE:
<221> NAME/KEY: misc_feature
<222> LOCATION: (1)..(60)
<223> OTHER INFORMATION: Xaa can be any naturally occurring amino acid

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

```
Xaa Xaa Xaa Xaa Xaa Xaa Xaa Xaa Xaa Xaa Xaa
    50                  55                  60

<210> SEQ ID NO 34
<211> LENGTH: 60
<212> TYPE: PRT
<213> ORGANISM: Artemia salina

<400> SEQUENCE: 34

Lys Ser Ile Pro Tyr Phe Trp Glu Lys Phe Asp Lys Glu Asn Tyr Ser
1               5                   10                  15

Ile Trp Tyr Ser Glu Tyr Lys Tyr Gln Asp Glu Leu Ala Lys Val Tyr
            20                  25                  30

Met Ser Cys Asn Leu Ile Thr Gly Met Phe Gln Arg Ile Glu Lys Met
        35                  40                  45

Arg Lys Gln Ala Phe Ala Ser Val Cys Val Phe Gly
    50                  55                  60

<210> SEQ ID NO 35
<211> LENGTH: 60
<212> TYPE: PRT
<213> ORGANISM: Mus musculus
<220> FEATURE:
<221> NAME/KEY: misc_feature
<222> LOCATION: (1)..(60)
<223> OTHER INFORMATION: Xaa can be any naturally occurring amino acid

<400> SEQUENCE: 35

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 36
<211> LENGTH: 60
<212> TYPE: PRT
<213> ORGANISM: Rattus norvegicus
<220> FEATURE:
<221> NAME/KEY: misc_feature
<222> LOCATION: (1)..(60)
<223> OTHER INFORMATION: Xaa can be any naturally occurring amino acid

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 37
<211> LENGTH: 60
<212> TYPE: PRT
<213> ORGANISM: Artemia salina

<400> SEQUENCE: 37
```

-continued

```
Glu Asp Asn Asp Ser Ser Ile Ser Gly Ile Trp Val Trp Arg Gly Gln
1               5                   10                  15

Asp Leu Ala Phe Lys Leu Ser Pro Asp Trp Gln Ile Asp Tyr Glu Ser
            20                  25                  30

Tyr Asp Trp Lys Lys Leu Asp Pro Asp Ala Gln Glu Thr Lys Asp Leu
        35                  40                  45

Val Thr Gln Tyr Phe Thr Trp Thr Gly Thr Asp Lys
    50                  55                  60
```

<210> SEQ ID NO 38
<211> LENGTH: 12
<212> TYPE: PRT
<213> ORGANISM: Mus musculus
<220> FEATURE:
<221> NAME/KEY: misc_feature
<222> LOCATION: (1)..(12)
<223> OTHER INFORMATION: Xaa can be any naturally occurring amino acid

<400> SEQUENCE: 38

```
Xaa Xaa Xaa Xaa Xaa Xaa Xaa Xaa Xaa Xaa Xaa Xaa
1               5                   10
```

<210> SEQ ID NO 39
<211> LENGTH: 12
<212> TYPE: PRT
<213> ORGANISM: Rattus norvegicus
<220> FEATURE:
<221> NAME/KEY: misc_feature
<222> LOCATION: (1)..(12)
<223> OTHER INFORMATION: Xaa can be any naturally occurring amino acid

<400> SEQUENCE: 39

```
Xaa Xaa Xaa Xaa Xaa Xaa Xaa Xaa Xaa Xaa Xaa Xaa
1               5                   10
```

<210> SEQ ID NO 40
<211> LENGTH: 12
<212> TYPE: PRT
<213> ORGANISM: Artemia salina

<400> SEQUENCE: 40

```
Gln Gly Arg Lys Phe Asn Gln Gly Lys Ile Phe Lys
1               5                   10
```

<210> SEQ ID NO 41
<211> LENGTH: 60
<212> TYPE: PRT
<213> ORGANISM: Caenorhabditis elegans
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid

<400> SEQUENCE: 41

```
Xaa Xaa Xaa Xaa Asn Phe Asp Xaa Xaa Xaa Lys Lys Thr Val Glu Gln
1               5                   10                  15

Tyr Lys Xaa Xaa Asn Glu Leu Asn Gly Gln Leu Gln Val Leu Asp Arg
            20                  25                  30
```

-continued

Val Leu Val Lys Lys Thr Tyr Leu Val Gly Glu Arg Leu Ser Leu Ala
            35                  40                  45

Asp Val Ser Val Ala Leu Asp Leu Leu Pro Ala Phe
    50                  55                  60

<210> SEQ ID NO 42
<211> LENGTH: 60
<212> TYPE: PRT
<213> ORGANISM: Homo sapien

<400> SEQUENCE: 42

Met Glu His Thr Glu Ile Asp His Trp Leu Glu Phe Ser Ala Thr Lys
1               5                   10                  15

Leu Ser Ser Cys Asp Ser Phe Thr Ser Thr Ile Asn Glu Leu Asn His
            20                  25                  30

Cys Leu Ser Leu Arg Thr Tyr Leu Val Gly Asn Ser Leu Ser Leu Ala
            35                  40                  45

Asp Leu Cys Val Trp Ala Thr Leu Lys Gly Asn Ala
    50                  55                  60

<210> SEQ ID NO 43
<211> LENGTH: 60
<212> TYPE: PRT
<213> ORGANISM: Caenorhabditis elegans
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid

<400> SEQUENCE: 43

Gln Tyr Val Leu Asp Ala Asn Ala Arg Lys Ser Ile Val Asn Val Thr
1               5                   10                  15

Arg Trp Phe Arg Thr Val Val Asn Gln Pro Ala Val Lys Glu Val Xaa
            20                  25                  30

Xaa Leu Gly Glu Val Ser Leu Ala Ser Ser Xaa Val Ala Xaa Gln Phe
            35                  40                  45

Asn Gln Xaa Xaa Ala Lys Phe Thr Glu Leu Ser Xaa
    50                  55                  60

<210> SEQ ID NO 44
<211> LENGTH: 60
<212> TYPE: PRT
<213> ORGANISM: Homo sapien

<400> SEQUENCE: 44

Ala Trp Gln Glu Gln Leu Lys Gln Lys Lys Ala Pro Val His Val Lys
1               5                   10                  15

Arg Trp Phe Gly Phe Leu Glu Ala Gln Gln Ala Phe Gln Ser Val Gly
            20                  25                  30

-continued

```
Thr Lys Trp Asp Val Ser Thr Thr Lys Ala Arg Val Ala Pro Glu Lys
         35                  40                  45

Lys Gln Asp Val Gly Lys Phe Val Glu Leu Pro Gly
 50                  55                  60

<210> SEQ ID NO 45
<211> LENGTH: 60
<212> TYPE: PRT
<213> ORGANISM: Caenorhabditis elegans
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (32)..(36)
<223> OTHER INFORMATION: Xaa can be any naturally occurring amino acid
<220> FEATURE:
<221> NAME/KEY: misc_feature
<222> LOCATION: (38)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid

<400> SEQUENCE: 45

Xaa Xaa Xaa Ala Lys Val Ala Lys Ser Ala Pro Lys Ala Glu Lys Pro
 1               5                  10                  15

Lys Lys Glu Ala Lys Pro Ala Ala Ala Xaa Xaa Ala Gln Pro Xaa
         20                  25                  30

Xaa Xaa Xaa Xaa Glu Xaa Xaa Xaa Xaa Xaa Xaa Asp Asp Xaa Glu
         35                  40                  45

Pro Lys Glu Glu Lys Ser Xaa Lys Asp Pro Xaa Xaa
 50                  55                  60

<210> SEQ ID NO 46
<211> LENGTH: 60
<212> TYPE: PRT
<213> ORGANISM: Homo sapien

<400> SEQUENCE: 46

Ala Glu Met Gly Lys Val Thr Val Arg Phe Pro Pro Glu Ala Ser Gly
 1               5                  10                  15

Tyr Leu His Ile Gly His Ala Lys Ala Ala Leu Leu Asn Gln His Tyr
         20                  25                  30

Gln Val Asn Phe Lys Gly Lys Leu Ile Met Arg Phe Asp Asp Thr Asn
         35                  40                  45

Pro Glu Lys Glu Lys Glu Asp Phe Glu Lys Val Ile
 50                  55                  60

<210> SEQ ID NO 47
<211> LENGTH: 60
<212> TYPE: PRT
```

-continued

<213> ORGANISM: Oryctolagus cuniculus

<400> SEQUENCE: 47

Met Ala Ala Gly Thr Leu Tyr Thr Tyr Pro Glu Asn Trp Arg Ala Phe
1               5                   10                  15

Lys Ala Leu Ile Ala Ala Gln Tyr Ser Gly Ala Gln Val Arg Val Leu
            20                  25                  30

Ser Ala Pro Pro His Phe His Phe Gly Gln Thr Asn Arg Thr Pro Glu
        35                  40                  45

Phe Leu Arg Lys Phe Pro Ala Gly Lys Val Pro Ala
    50                  55                  60

<210> SEQ ID NO 48
<211> LENGTH: 60
<212> TYPE: PRT
<213> ORGANISM: Zea mays
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid

<400> SEQUENCE: 48

Xaa Ala Thr Pro Ala Val Lys Val Tyr Gly Trp Ala Ile Ser Pro Phe
1               5                   10                  15

Val Ser Arg Ala Leu Leu Ala Leu Glu Glu Ala Gly Val Asp Tyr Glu
            20                  25                  30

Leu Val Pro Met Ser Arg Gln Asp Gly Asp Xaa His Arg Arg Pro Glu
        35                  40                  45

His Leu Ala Arg Asn Pro Phe Gly Lys Val Pro Val
    50                  55                  60

<210> SEQ ID NO 49
<211> LENGTH: 60
<212> TYPE: PRT
<213> ORGANISM: Oryctolagus cuniculus
<220> FEATURE:
<221> NAME/KEY: misc_feature
<222> LOCATION: (21)..(24)
<223> OTHER INFORMATION: Xaa can be any naturally occurring amino acid
<220> FEATURE:
<221> NAME/KEY: misc_feature
<222> LOCATION: (57)..(60)
<223> OTHER INFORMATION: Xaa can be any naturally occurring amino acid

<400> SEQUENCE: 49

Phe Glu Gly Asp Asp Gly Phe Cys Val Phe Glu Ser Asn Ala Ile Ala
1               5                   10                  15

Tyr Tyr Val Ser Xaa Xaa Xaa Xaa Asn Glu Glu Leu Arg Gly Ser Thr
            20                  25                  30

Pro Glu Ala Ala Ala Gln Val Val Gln Trp Val Ser Phe Ala Asp Ser
        35                  40                  45

Asp Ile Val Pro Pro Ala Ser Thr Xaa Xaa Xaa Xaa
    50                  55                  60

<210> SEQ ID NO 50
<211> LENGTH: 60
<212> TYPE: PRT
<213> ORGANISM: Zea mays
<220> FEATURE:
<221> NAME/KEY: misc_feature

```
<222> LOCATION: (3)..(3)
<223> OTHER INFORMATION: Xaa can be any naturally occurring amino acid

<400> SEQUENCE: 50

Leu Glu Xaa Asp Gly Asp Leu Thr Leu Phe Glu Ser Arg Ala Ile Ala
1               5                   10                  15

Arg His Val Leu Arg Lys His Lys Pro Glu Leu Leu Gly Gly Gly Arg
                20                  25                  30

Leu Glu Gln Thr Ala Met Val Asp Val Trp Leu Glu Val Glu Ala His
            35                  40                  45

Gln Leu Ser Pro Pro Ala Ile Ala Ile Val Val Glu
        50                  55                  60

<210> SEQ ID NO 51
<211> LENGTH: 60
<212> TYPE: PRT
<213> ORGANISM: Oryctolagus cuniculus

<400> SEQUENCE: 51

Trp Val Phe Pro Thr Leu Gly Ile Met His His Asn Lys Gln Ala Thr
1               5                   10                  15

Glu Asn Ala Lys Glu Glu Val Lys Arg Ile Leu Gly Leu Leu Asp Ala
                20                  25                  30

His Leu Lys Thr Arg Thr Phe Leu Val Gly Glu Arg Val Thr Leu Ala
            35                  40                  45

Asp Ile Thr Val Val Cys Thr Leu Leu Trp Leu Tyr
        50                  55                  60

<210> SEQ ID NO 52
<211> LENGTH: 60
<212> TYPE: PRT
<213> ORGANISM: Zea mays
<220> FEATURE:
<221> NAME/KEY: misc_feature
<222> LOCATION: (54)..(54)
<223> OTHER INFORMATION: Xaa can be any naturally occurring amino acid

<400> SEQUENCE: 52

Cys Val Phe Ala Pro Phe Leu Gly Arg Glu Arg Asn Gln Ala Val Val
1               5                   10                  15

Asp Glu Asn Val Glu Lys Leu Lys Lys Val Leu Glu Val Tyr Glu Ala
                20                  25                  30

Arg Leu Ala Thr Cys Thr Tyr Leu Ala Gly Asp Phe Leu Ser Leu Ala
            35                  40                  45

Asp Leu Ser Pro Phe Xaa Thr Ile Met His Cys Leu
        50                  55                  60

<210> SEQ ID NO 53
<211> LENGTH: 60
<212> TYPE: PRT
<213> ORGANISM: Oryctolagus cuniculus

<400> SEQUENCE: 53

Lys Gln Val Leu Glu Pro Ser Phe Arg Gln Ala Phe Pro Asn Thr Asn
1               5                   10                  15

Arg Trp Phe Leu Thr Cys Ile Asn Gln Pro Gln Phe Arg Ala Val Leu
                20                  25                  30

Gly Glu Val Lys Leu Cys Glu Lys Met Ala Gln Phe Asp Ala Lys Lys
            35                  40                  45

Phe Ala Glu Ser Gln Pro Lys Lys Asp Thr Pro Arg
```

<210> SEQ ID NO 54
<211> LENGTH: 60
<212> TYPE: PRT
<213> ORGANISM: Zea mays
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (33)..(39)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid

<400> SEQUENCE: 54

Met Ala Thr Glu Tyr Ala Ala Leu Val His Ala Leu Pro His Val Ser
1               5                   10                  15

Ala Trp Trp Gln Gly Leu Ala Ala Arg Pro Xaa Xaa Xaa Ala Ala Asn
            20                  25                  30

Xaa Xaa Xaa Xaa Xaa Xaa Xaa Lys Val Ala Gln Phe Xaa Xaa Met Pro
        35                  40                  45

Val Gly Ala Gly Ala Pro Lys Glu Gln Glu Xaa Xaa
    50                  55                  60

<210> SEQ ID NO 55
<211> LENGTH: 30
<212> TYPE: PRT
<213> ORGANISM: Caenorhabditis elegans

<400> SEQUENCE: 55

Ile Phe Asp Asn Thr Asn Asp Leu Val Ala Ser Leu Leu Gly Ile Ser
1               5                   10                  15

Ser Ile Thr Val Tyr Arg Lys Arg Lys Arg Ile Gly Glu Glu
            20                  25                  30

<210> SEQ ID NO 56
<211> LENGTH: 30
<212> TYPE: PRT
<213> ORGANISM: Caenorhabditis elegans

<400> SEQUENCE: 56

Tyr Leu Ser Gly Ser Thr Arg Ala Lys Leu Ala Glu Ser Leu Gly Leu
1               5                   10                  15

Ser Asp Asn Gln Val Lys Val Trp Phe Gln Asn Arg Arg Thr
            20                  25                  30

<210> SEQ ID NO 57
<211> LENGTH: 30
<212> TYPE: PRT
<213> ORGANISM: Caenorhabditis elegans

<400> SEQUENCE: 57

Ile Ser Arg Ser Thr Ala Lys Glu Val Ala Thr Ala Arg Gly Ile Ser
1               5                   10                  15

Glu Gly Thr Val Tyr Ser Tyr Leu Ala Met Ala Val Glu Lys
            20                  25                  30

```
<210> SEQ ID NO 58
<211> LENGTH: 30
<212> TYPE: PRT
<213> ORGANISM: Caenorhabditis elegans

<400> SEQUENCE: 58

Leu Ser Ala Tyr Thr Ile Ser Asp Leu Ala Lys His Phe Asn Val Ser
1               5                   10                  15

Lys Ile Glu Ile Leu Lys Ile Asp Ile Glu Gly Ala Glu Leu
            20                  25                  30

<210> SEQ ID NO 59
<211> LENGTH: 30
<212> TYPE: PRT
<213> ORGANISM: Caenorhabditis elegans

<400> SEQUENCE: 59

Asn Glu Val Leu Asn Leu Asn Glu Val Ala Lys Glu Leu Asn Ile Ser
1               5                   10                  15

Lys Arg Arg Val Tyr Asp Val Ile Asn Val Leu Glu Gly Leu
            20                  25                  30
```